(12) United States Patent
Simon et al.

(10) Patent No.: US 9,233,258 B2
(45) Date of Patent: Jan. 12, 2016

(54) MAGNETIC STIMULATION DEVICES AND METHODS OF THERAPY

(71) Applicant: Electrocore, LLC, Basking Ridge, NJ (US)

(72) Inventors: Bruce J. Simon, Mountain Lakes, NJ (US); Joseph P. Errico, Warren, NJ (US); Jonn T. Raffle, Austin, TX (US)

(73) Assignee: Electrocore, LLC, Basking Ridge, NJ (US)

(*) Notice: Subject to any disclaimer, the term of this patent is extended or adjusted under 35 U.S.C. 154(b) by 0 days.

(21) Appl. No.: 14/636,498

(22) Filed: Mar. 3, 2015

(65) Prior Publication Data

US 2015/0165226 A1    Jun. 18, 2015

Related U.S. Application Data

(60) Division of application No. 13/938,931, filed on Jul. 10, 2013, now Pat. No. 8,972,004, which is a division of application No. 12/964,050, filed on Dec. 9, 2010, now abandoned, said application No. 13/938,931 is a (Continued)

(51) Int. Cl.
*A61N 1/36* (2006.01)
*A61N 2/02* (2006.01)

(Continued)

(52) U.S. Cl.
CPC .. *A61N 2/02* (2013.01); *A61N 1/36* (2013.01); *A61N 1/40* (2013.01); *A61N 2/006* (2013.01); *A61N 1/36114* (2013.01)

(58) Field of Classification Search
None
See application file for complete search history.

(56) References Cited

U.S. PATENT DOCUMENTS

| | | |
|---|---|---|
| 3,590,810 A | 7/1971 | Kopecky |
| 4,196,737 A | 4/1980 | Bevilacqua |

(Continued)

FOREIGN PATENT DOCUMENTS

| | | |
|---|---|---|
| WO | WO 93/01862 | 2/1993 |
| WO | WO 2009/021080 | 2/2009 |

(Continued)

OTHER PUBLICATIONS

Greicius et al., Functional connectivity in the resting brain: A network analysis of the default mode hypothesis, PNAS, Jan. 2003, vol. 100, No. 1, pp. 253-258.

(Continued)

*Primary Examiner* — Brian T Gedeon
*Assistant Examiner* — Ankit Tejani
(74) *Attorney, Agent, or Firm* — Dentons US LLP

(57) ABSTRACT

Devices and systems are disclosed for the non-invasive treatment of medical conditions through delivery of energy to target tissue, comprising a source of electrical power, a magnetically permeable toroidal core, and a coil that is wound around the core. The coil and core are embedded in a continuous electrically conducting medium, which is adapted to have a shape that conforms to the contour of an arbitrarily oriented target body surface of a patient. The conducting medium is applied to that surface by any of several disclosed methods, and the source of power supplies a pulse of electric charge to the coil, such that the coil induces an electric current and/or an electric field within the patient, thereby stimulating tissue and/or one or more nerve fibers within the patient. The invention shapes an elongated electric field of effect that can be oriented parallel to a long nerve. In one embodiment, the device comprises two toroidal cores that lie adjacent to one another.

13 Claims, 9 Drawing Sheets

Related U.S. Application Data continuation-in-part of application No. 12/859,568, filed on Aug. 19, 2010, now Pat. No. 9,037,247, which is a continuation-in-part of application No. 12/408,131, filed on Mar. 20, 2009, now Pat. No. 8,812,112, which is a continuation-in-part of application No. 11/591,340, filed on Nov. 1, 2006, now Pat. No. 7,747,324.

(60) Provisional application No. 61/415,469, filed on Nov. 19, 2010, provisional application No. 60/814,313, filed on Jun. 16, 2006, provisional application No. 60/786,564, filed on Mar. 28, 2006, provisional application No. 60/772,361, filed on Feb. 10, 2006, provisional application No. 60/736,002, filed on Nov. 10, 2005, provisional application No. 60/736,001, filed on Nov. 10, 2005.

(51) Int. Cl.
*A61N 1/40* (2006.01)
*A61N 2/00* (2006.01)

(56) References Cited

U.S. PATENT DOCUMENTS

| | | | |
|---|---|---|---|
| 5,458,141 A | 10/1995 | Neil | |
| 5,487,759 A | 1/1996 | Bastyr et al. | |
| 5,782,874 A | 7/1998 | Loos | |
| 5,899,922 A | 5/1999 | Loos | |
| 5,983,131 A | 11/1999 | Weaver et al. | |
| 6,074,385 A * | 6/2000 | Klopotek | A61B 18/14 128/898 |
| 6,341,236 B1 | 1/2002 | Osorio et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 7,797,041 B2 | 9/2010 | Libbus et al. | |
| 2002/0099417 A1 | 7/2002 | Naritoku et al. | |
| 2002/0183237 A1 | 12/2002 | Puskas | |
| 2003/0212395 A1 * | 11/2003 | Woloszko et al. | 606/41 |
| 2004/0122281 A1 * | 6/2004 | Fischell et al. | 600/13 |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 * | 5/2005 | Fox et al. | 600/13 |
| 2005/0137644 A1 | 6/2005 | Boveja et al. | |
| 2005/0187590 A1 | 8/2005 | Boveja et al. | |
| 2006/0074284 A1 | 4/2006 | Juola et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2006/0264692 A1 * | 11/2006 | Riehl | A61N 2/006 600/13 |
| 2007/0027496 A1 | 2/2007 | Parnis et al. | |
| 2007/0038264 A1 | 2/2007 | Jaax et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0156182 A1 | 7/2007 | Castel et al. | |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0132964 A1 | 6/2008 | Cohen et al. | |
| 2008/0177190 A1 | 7/2008 | Libbus et al. | |
| 2008/0208266 A1 | 8/2008 | Lesser et al. | |
| 2008/0306325 A1 | 12/2008 | Burnett et al. | |
| 2009/0157149 A1 | 6/2009 | Wahlgren et al. | |
| 2009/0234419 A1 | 9/2009 | Maschino et al. | |
| 2009/0287035 A1 | 11/2009 | Dietrich et al. | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |

FOREIGN PATENT DOCUMENTS

| | | |
|---|---|---|
| WO | WO 2009/064641 | 5/2009 |
| WO | WO 2009/135693 | 11/2009 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

\* cited by examiner

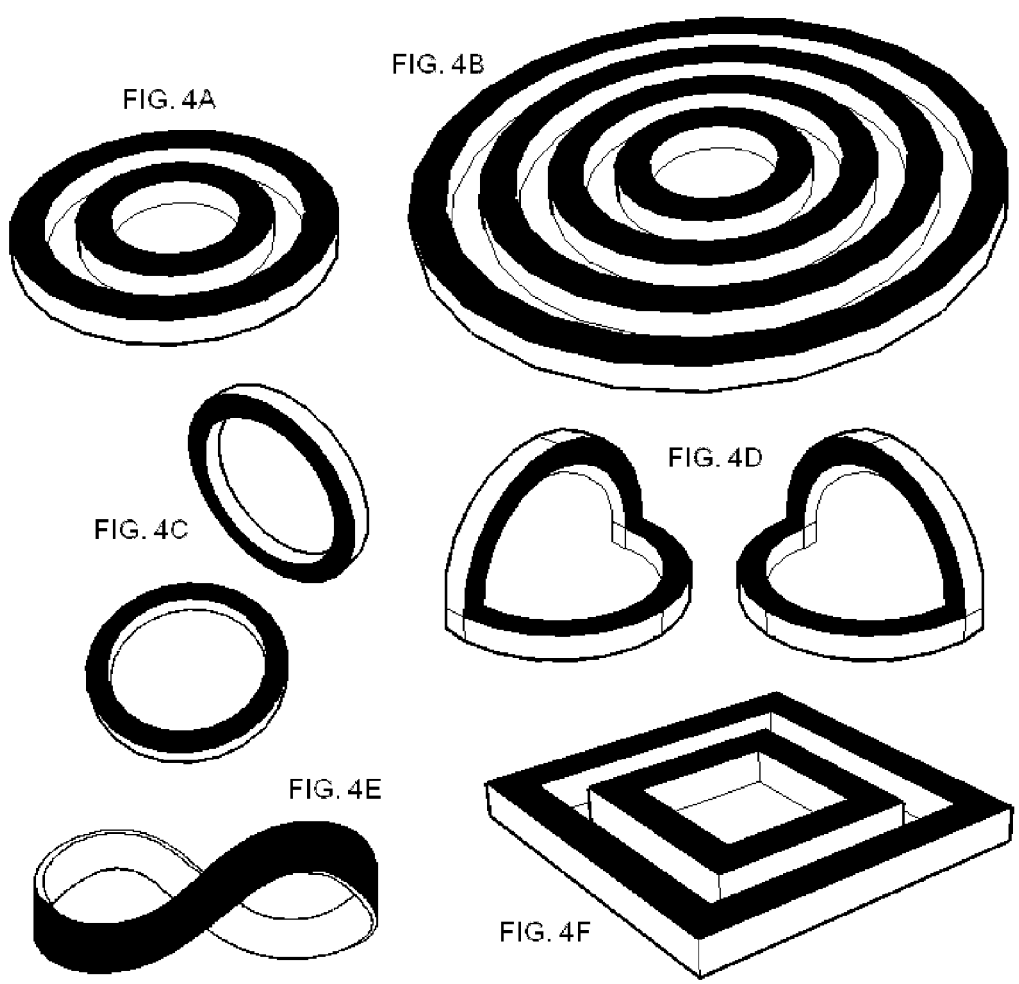

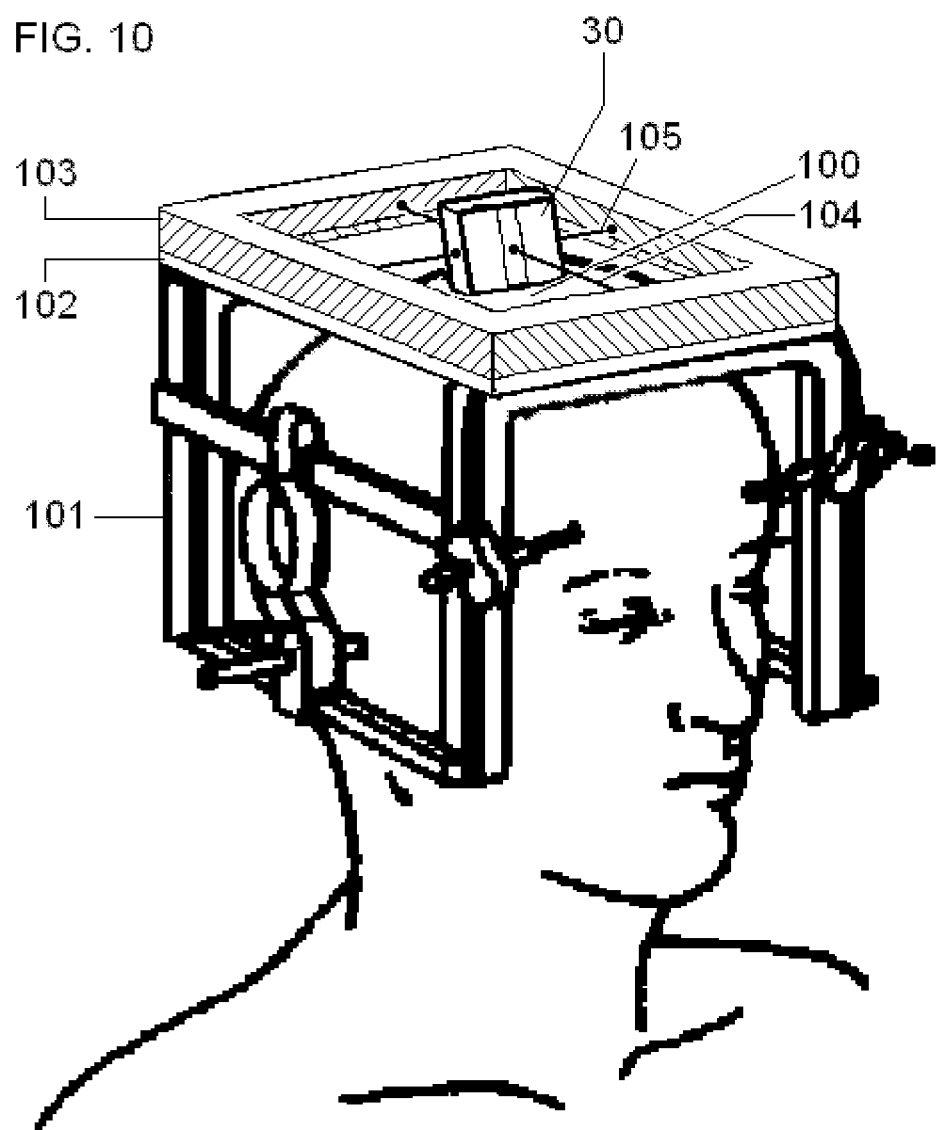

MAGNETIC STIMULATION DEVICES AND METHODS OF THERAPY

CROSS REFERENCE TO RELATED APPLICATIONS

The present application is a Divisional of U.S. patent application Ser. No. 13/938,931 filed 10 Jul. 2013, which is a Divisional of U.S. patent application Ser. No. 12/964,050 filed 9 Dec. 2010, which claims the benefit of U.S. Provisional Application Ser. No. 61/415,469 filed 19 Nov. 2010; and is a Continuation in Part of U.S. patent application Ser. No. 12/859,568 filed 19 Aug. 2010, which is a Continuation in Part of U.S. patent application Ser. No. 12/408,131 filed 20 Mar. 2009, now U.S. Pat. No. 8,812,112 issued 19 Aug. 2014, which is a Continuation in Part of U.S. patent application Ser. No. 11/591,340, filed 1 Nov. 2006, now U.S. Pat. No 7,747,324 issued 29 Jun. 2010, which claims the benefit of U.S. Provisional Application Ser. Nos. 60/814,313 filed 16 Jun. 2006, 60/786,564 filed 28 Mar. 2006, 60/772,361 filed 10 Feb. 2006, 60/736,002 filed 10 Nov. 2005, and 60/736,001 filed 10 Nov. 2005; each of which is incorporated herein by reference in its entirety.

BACKGROUND OF THE INVENTION

The field of the present invention relates to the delivery of energy impulses (and/or fields) to bodily tissues for therapeutic purposes. It relates more specifically to toroidal magnetic stimulation devices, as well as to non-invasive methods for treating medical conditions using energy that is delivered by such devices. The medical conditions include, but are not limited to, post-operative ileus, neurodegenerative disorders (such as Alzheimer's disease), post-operative cognitive dysfunction (POCD), post-operative delirium (POD), dementia, rheumatoid arthritis, acute and chronic depression, epilepsy, Parkinson's disease, multiple sclerosis (MS), bronchoconstriction associated with asthma, anaphylaxis or COPD, sepsis or septic shock, hypovolemia or hypovolemic shock, orthostatic hypotension, hypertension, urinary incontinence and/or overactive bladder, and sphincter of Oddi dysfunction.

Treatments for various infirmities sometime require the destruction of otherwise healthy tissue in order to produce a beneficial effect. Malfunctioning tissue is identified and then lesioned or otherwise compromised in order to produce a beneficial outcome, rather than attempting to repair the tissue to its normal functionality. A variety of techniques and mechanisms have been designed to produce focused lesions directly in target nerve tissue, but collateral damage is inevitable.

Other treatments for malfunctioning tissue can be medicinal in nature, but in many cases the patients become dependent upon artificially synthesized chemicals. Examples of this are anti-asthma drugs such as albuterol, proton pump inhibitors such as omeprazole (PRILOSEC®), spastic bladder relievers such as DITROPAN®, and cholesterol reducing drugs such as LIPITOR® and ZOCOR®. In many cases, these medicinal approaches have side effects that are either unknown or quite significant. For example, at least one popular diet pill of the late 1990's was subsequently found to cause heart attacks and strokes. Unfortunately, the beneficial outcomes of surgery and medicines are often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue holds significant promise for the treatment of many ailments, because such stimulation is generally a wholly reversible and non-destructive treatment.

Nerve stimulation is thought to be accomplished directly or indirectly by depolarizing a nerve membrane, causing the discharge of an action potential; or by hyperpolarization of a nerve membrane, preventing the discharge of an action potential. Such stimulation may occur after electrical energy, or also other forms of energy, are transmitted to the vicinity of a nerve [F. RATTAY. The basic mechanism for the electrical stimulation of the nervous system. Neuroscience Vol. 89, No. 2, pp. 335-346, 1999; Thomas HEIMBURG and Andrew D. Jackson. On soliton propagation in biomembranes and nerves. PNAS vol. 102 (no. 28, Jul. 12, 2005): 9790-9795]. Nerve stimulation may be measured directly as an increase, decrease, or modulation of the activity of nerve fibers, or it may be inferred from the physiological effects that follow the transmission of energy to the nerve fibers.

Electrical stimulation of the brain with implanted electrodes has been approved for use in the treatment of various conditions, including pain and movement disorders such as essential tremor and Parkinson's disease. The principle underlying these approaches involves disruption and modulation of hyperactive neuronal circuit transmission at specific sites in the brain. Unlike potentially dangerous lesioning procedures in which aberrant portions of the brain are physically destroyed, electrical stimulation is achieved by implanting electrodes at these sites. The electrodes are used first to sense aberrant electrical signals and then to send electrical pulses to locally disrupt pathological neuronal transmission, driving it back into the normal range of activity. These electrical stimulation procedures, while invasive, are generally conducted with the patient conscious and a participant in the surgery.

Brain stimulation, and deep brain stimulation in particular, is not without some drawbacks. The procedure requires penetrating the skull, and inserting an electrode into brain matter using a catheter-shaped lead, or the like. While monitoring the patient's condition (such as tremor activity, etc.), the position of the electrode is adjusted to achieve significant therapeutic potential. Next, adjustments are made to the electrical stimulus signals, such as frequency, periodicity, voltage, current, etc., again to achieve therapeutic results. The electrode is then permanently implanted, and wires are directed from the electrode to the site of a surgically implanted pacemaker. The pacemaker provides the electrical stimulus signals to the electrode to maintain the therapeutic effect. While the therapeutic results of deep brain stimulation are promising, there are significant complications that arise from the implantation procedure, including stroke induced by damage to surrounding tissues and the neuro-vasculature.

One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat.

No. 6,738,667 to DENO, et al., the disclosure of which is incorporated herein by reference).

Another application of electrical stimulation of nerves has been the treatment of radiating pain in the lower extremities by stimulating the sacral nerve roots at the bottom of the spinal cord (see U.S. Pat. No. 6,871,099 to WHITEHURST, et al., the disclosure of which is incorporated herein by reference).

The present disclosure involves devices and medical procedures that stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that invasive procedures do involve inserting a substance or device into or through the skin or into an internal body cavity beyond a body orifice.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are sometimes painless or only minimally painful and may be performed without the need for even local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace, and the cost of non-invasive procedures may be reduced relative to comparable invasive procedures.

For example, transcutaneous electrical nerve stimulation (TENS) is non-invasive because it involves attaching electrodes to the surface of the skin (or using a form-fitting conductive garment) without breaking the skin. In contrast, percutaneous electrical stimulation of a nerve is minimally invasive because it involves the introduction of an electrode under the skin, via needle-puncture of the skin. Both TENS and percutaneous electrical stimulation can be to some extent unpleasant or painful, in the experience of patients that undergo such procedures. In the case of TENS, as the depth of penetration of the stimulus under the skin is increased, any pain will generally begin or increase.

The form of non-invasive electrical stimulation with which the present application is primarily concerned is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body, inducing at a distance an electric field and electric current within electrically-conducting bodily tissue. Because the induced electric field and induced current depend not only upon current being passed through wire of the coil, but also upon the permeability of core material around which the coil may be wound, the term coil as used herein refers not only to the current-carrying wire, but also to the core material, unless otherwise indicated.

Large, pulsed magnetic fields (PMF) can induce significant electric fields in conducting media, including human tissue. Particular waveforms and amplitudes can stimulate action potentials in nerves, both in vitro and in vivo. Due to the noninvasive nature of the stimulation, PMF devices have found utility in several clinical applications, both therapeutically, e.g., for treating depression via transcranial magnetic stimulation (TMS), and diagnostically, for peripheral nerve stimulation. It is an objective of the present invention to use magnetic stimulation to produce significantly less pain or discomfort, as compared with that experienced by the patient undergoing a treatment with TENS, for a given depth of stimulus penetration. Or conversely, for a given amount of pain or discomfort on the part of the patient (e.g., the threshold at which such discomfort or pain begins), an objective of the present invention is to achieve a greater depth of penetration of the stimulus under the skin.

The principle of operation of magnetic stimulation, along with a description of commercially available equipment and a list of medical applications of magnetic stimulation, is reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006. The types of the magnetic stimulator coils that are described there include circular, parabolic, figure-of-eight (butterfly), and custom designs. Additional types of the magnetic stimulator coils are described in U.S. Pat. No. 6,179,770, entitled Coil assemblies for magnetic stimulators, to MOULD; as well as in Kent DAVEY. Magnetic Stimulation Coil and Circuit Design. IEEE Transactions on Biomedical Engineering, Vol. 47 (No. 11, November 2000): 1493-1499 and in HSU KH, Nagarajan S S, Durand D M. Analysis of efficiency of magnetic stimulation. IEEE Trans Biomed Eng. 2003 November; 50 (11):1276-85.

The circuits that are used to send pulses or other waveforms through magnetic stimulator coils are also described by HOVEY and Jalinous in The Guide to Magnetic Stimulation that was cited above. Custom magnetic stimulator circuits for control, impulse generator and power supply have also been described [Eric BASHAM, Zhi Yang, Natalia Tchemodanov, and Wentai Liu. Magnetic Stimulation of Neural Tissue: Techniques and System Design. pp 293-352, In: Implantable Neural Prostheses 1, Devices and Applications, D. Zhou and E. Greenbaum, eds., New York: Springer (2009); U.S. Pat. No. 7,744,523, entitled Drive circuit for magnetic stimulation, to EPSTEIN; U.S. Pat. No. 5,718,662, entitled Apparatus for the magnetic stimulation of cells or tissue, to JANILOUS; U.S. Pat. No. 5,766,124, entitled Magnetic stimulator for neuro-muscular tissue, to POLSON].

As described in the above-cited publications, the circuits for magnetic stimulators are generally complex and expensive. They use a high current impulse generator that may produce discharge currents of 5,000 amps or more, which is passed through the stimulator coil, and which thereby produces a magnetic pulse. Typically, a transformer charges a capacitor in the impulse generator, which also contains circuit elements that limit the effect of undesirable electrical transients. Charging of the capacitor is under the control of a control unit, which accepts information such as the capacitor voltage, power and other parameters set by the user, as well as from various safety interlocks within the equipment that ensure proper operation, and the capacitor is then discharged through the coil via an electronic switch (e.g., a controlled rectifier) when the user wishes to apply the stimulus. Greater flexibility is obtained by adding to the impulse generator a bank of capacitors that can be discharged at different times. Thus, higher impulse rates may be achieved by discharging capacitors in the bank sequentially, such that recharging of capacitors is performed while other capacitors in the bank are being discharged. Furthermore, by discharging some capacitors while the discharge of other capacitors is in progress, by discharging the capacitors through resistors having variable resistance, and by controlling the polarity of the discharge, the control unit may synthesize pulse shapes that approximate an arbitrary function.

Another practical disadvantage of magnetic stimulator coils is that they overheat when used over an extended period of time, because large coil currents are required to reach threshold electric fields in the stimulated tissue. At high repetition rates, currents can heat the coils to unacceptable levels in seconds to minutes, depending on the power levels and pulse durations and rates. Accordingly, coil-cooling equipment is used, which adds complexity to the magnetic stimulator coils. Two approaches to overcome heating are to cool the coils with flowing water or air or to increase the magnetic fields using ferrite cores (thus allowing smaller currents). For some applications where relatively long treatment times at high stimulation frequencies may be required, e.g. treating asthma by stimulating the vagus nerve, neither of these two approaches may be adequate. Water-cooled coils overheat in a few minutes. Ferrite core coils heat more slowly due to the lower currents and heat capacity of the ferrite core, but they also cool slowly and do not allow for water-cooling because the ferrite core occupies the volume where the cooling water would flow. One solution to this problem is to use a core that contains ferrofluids [U.S. Pat. No. 7,396,326 and published applications US20080114199, US20080177128, and US20080224808, all entitled Ferrofluid cooling and acoustical noise reduction in magnetic stimulators, respectively to GHIRON et al., RIEHL et al., RIEHL et al. and GHIRON et al.]. However, even the use of ferrofluids may be inadequate when long treatment times at high stimulation frequencies may be required.

Another problem that is sometimes encountered during magnetic stimulation is the unpleasantness or pain that is experienced by the patient in the vicinity of the stimulated tissue. Little is known about the mechanism that produces the pain, although it is generally recognized that magnetic stimulation produces less pain than its electrode-based counterpart. Most investigations that address this question examine pain associated with transcranial stimulation.

ANDERSON et al found that when magnetic stimulation is repeated over the course of multiple sessions, the patients adapt to the pain and exhibit progressively less discomfort [Berry S. ANDERSON, Katie Kavanagh, Jeffrey J. Borckardt, Ziad H. Nahas, Samet Kose, Sarah H. Lisanby, William M. McDonald, David Avery, Harold A. Sackeim, and Mark S. George. Decreasing Procedural Pain Over Time of Left Prefrontal rTMS for Depression: Initial Results from the Open-Label Phase of a Multisite Trial (OPT-TMS). Brain Stimul. 2009 Apr. 1; 2(2): 88-92]. Other than waiting for the patient to adapt, strategies to reduce the pain include: use of anesthetics placed on or injected into the skin near the stimulation and placement of foam pads on the skin at the site of stimulation [Jeffrey J. BORCKARRDT, Arthur R. Smith, Kelby Hutcheson, Kevin Johnson, Ziad Nahas, Berry Anderson, M. Bret Schneider, Scott T. Reeves, and Mark S. George. Reducing Pain and Unpleasantness During Repetitive Transcranial Magnetic Stimulation. Journal of ECT 2006; 22:259-264], use of nerve blockades [V. HAKKINEN, H. Eskola, A. Yli-Hankala, T. Nurmikko and S. Kolehmainen. Which structures are sensitive to painful transcranial stimulation? Electromyogr. clin. Neurophysiol. 1995, 35:377-383], the use of very short stimulation pulses [V. SUIHKO. Modelling the response of scalp sensory receptors to transcranial electrical stimulation. Med. Biol. Eng. Comput., 2002, 40, 395-401], and providing patients with the amount of information that suits their personalities [Anthony DELITTO, Michael J Strube, Arthur D Shulman, Scott D Minor. A Study of Discomfort with Electrical Stimulation. Phys. Ther. 1992; 72:410-424]. U.S. Pat. No. 7,614,996, entitled Reducing discomfort caused by electrical stimulation, to RIEHL discloses the application of a secondary stimulus to counteract what would otherwise be an uncomfortable primary stimulus. However, these methods of reducing pain or discomfort on the part of the stimulated patient are not always successful or practical.

SUMMARY OF THE INVENTION

The present invention discloses devices and methods for the non-invasive treatment of medical conditions, utilizing an energy source that transmits energy non-invasively to bodily tissue. In particular, the device can transmit energy to, or in close proximity to, one or more selected nerves to temporarily stimulate, block and/or modulate electrophysiological signals in the selected nerves.

In one aspect of the invention, an apparatus for applying energy transcutaneously to a target region within a patient comprises a source of energy for generating a magnetic field that is located essentially entirely exterior to an outer skin surface of the patient and a conduction medium through which an electrical current induced by the magnetic field penetrates the outer skin surface of the patient. The source of energy and the conduction medium are configured to shape the electrical field that is induced by the magnetic field, such that energy from the induced electric field and/or induced current is sufficient to modulate a nerve at the target region. The source of energy is preferably a source of electrical energy coupled to a coil housed within an enclosure that is configured to contain the magnetic field therein.

In one embodiment, the source of energy comprises a source of electrical energy coupled to first and second coils configured to generate first and second time-varying magnetic fields; each coil being housed within an enclosure configured to substantially confine the magnetic field therein. The first and second coils are preferably toroidal such that the first coil is configured to orient the first magnetic field in a first direction around the first toroid and the second coil is configured to orient the second magnetic field in a second direction around the second solenoid, and wherein the first and second directions are opposite. The conduction medium is preferably positioned in electrical contact to a portion of an outside surface of the enclosure to at least partially restrict the direction of the electric field. In an exemplary embodiment, the conduction medium comprises an electrically conductive fluid, such as a solution of electrolytes or a conductive gel, housed within the outer enclosure and at least In another aspect of the invention, a method is provided for selectively applying energy to a target region within a patient. The method includes generating a time-varying magnetic field that is located essentially entirely outside of the patient and shaping an electric field induced by the magnetic field. An electric current from the electric field is conducted through an outer skin surface of the patient to the target region to modulate a nerve at the target region. The target region is preferably at least approximately 1-2 cm below the outer skin surface and preferably about 2-5 cm below the outer skin surface. The electric field is constrained from modulating one or more nerves in a second region between the outer skin surface and the target region.

In one embodiment, the generating step comprises generating the time-varying magnetic field within a first enclosed coil and generating a second time-varying magnetic field within a second enclosed coil positioned near or adjacent to the first enclosed coil. In an alternative embodiment, the shaping step comprises positioning a conducting medium around a portion of the enclosed coil such that the direction of the electrical field is constrained within the conducting medium. In yet another embodiment, the shaping step comprises positioning an electrical insulator around a portion of the enclosed coil such that the component of the induced electric field normal to the surface of the insulator is zero.

In another aspect of the present invention, a device comprises a source of electrical power, a magnetically permeable toroidal core, and a coil that is wound around the core. The device also comprises a continuous electrically conducting medium in which the coil and core are embedded, wherein the conducting medium has a shape that conforms to the contour of an arbitrarily oriented target body surface of a patient when the medium is applied to the target body surface. The source of power supplies a pulse of electric charge to the coil, such that the coil induces an electric current and/or an electric field within the patient, thereby stimulating tissue and/or one or more nerve fibers within the patient.

Because coils of the device produce time-varying magnetic fields when time-varying currents are passed through the coils, and because the time-varying magnetic fields induce an electric current and/or an electric field within the patient, the device is known as a magnetic stimulator. Because the magnetically permeable cores of the device and their corresponding coils are in the shape of a toroid, the device is known as a toroidal magnetic stimulator. In one aspect of the invention, a toroidal core comprises a high-permeability material such as Supermendur, wherein current passing through the coil produces a magnetic field within the core of about 0.1 to 2 Tesla. Current passing through a coil may be about 0.5 to 20 amperes, typically 2 amperes, with voltages across each coil of 10 to 100 volts. The current is passed through the coils in bursts of pulses. The burst repeats at 1 Hz to 5000 Hz, preferably at 15-50 Hz. The pulses have duration of 20 to 1000 microseconds, preferably 200 microseconds and there may be 1 to 20 pulses per burst.

The disclosed invention shapes an elongated electric field of effect that can be oriented parallel to a long nerve. In a preferred embodiment, the device comprises two toroidal cores that lie side-by-side one another, around which coils are wound. In one embodiment, coils are wound with the same handedness around the cores, and current is passed in opposite directions through the coils. In another embodiment, coils are wound with the opposite handedness around the cores, and current is passed in the same direction through the coils. In other embodiments of the invention, the device comprises more than two toroids, and the shapes of the toroids may be configured to have non-planar or non-circular geometries.

In one embodiment of the present invention, the electrically conducting medium is contained within a chamber having apertures on its surface that are adapted to dispense the conducting medium through the apertures to the target surface of the patient. In another embodiment, interface material is interposed between the conducting medium and the target surface of a patient, such that the conducting medium leaks through the interface to make electrical contact with the skin of the patient. For example the interface material may be electrically conducting material that is hydrophilic, an electrically conducting hydrogel, or a material such as MYLAR® having a sub-micron thickness and a high dielectric constant, for example, a dielectric constant of about 3. In another embodiment of the invention, the conducting medium is contained within a conducting deformable elastomeric balloon.

In one embodiment of the present invention, the magnetic stimulator preferably operates to induce an electrical signal within the tissue, where the induced electrical signal has a frequency between about 1 Hz to 3000 Hz and a pulse duration of between about 10-1000 microseconds. By way of example, at least one induced electrical signal may be of a frequency between about 15 Hz to 35 Hz. By way of example, at least one induced electrical signal may have a pulsed on-time of between about 50 to 1000 microseconds, such as between about 100 to 300 microseconds. The induced electrical signal may have any desired waveform, which may be one or more of: a full or partial sinusoid, a square wave, a rectangular wave, and triangle wave.

In one aspect of the invention, the disclosed device is configured to induce a peak pulse voltage sufficient to produce an electric field in the vicinity of a nerve to cause the nerve to depolarize and reach a threshold for action potential propagation. By way of example, the threshold electric field for stimulation of nerve terminals may be about 8 V/m at 1000 Hz. For example, the device may induce an electric field within the patient of about 10 to 600 V/m and an electrical field with a gradient of greater than 2 V/m/mm.

In embodiments of methods that use the disclosed devices, a magnetic stimulator coil is positioned non-invasively on or above a target anatomical location, such as on or near a patient's neck, ankle, abdomen, or scalp, in the vicinity of nerves or tissue that control a physiological reflex or response. The electric field and/or eddy-currents induced as energy impulses by the coil of the magnetic stimulator create a field of effect that permeates the target nerve fibers or tissue and cause the stimulating, blocking, and/or modulation of signals to an end organ that is controlled by the stimulated nerves or tissue.

In one aspect of the present invention, a method of treating a medical condition comprises stimulating selected nerve fibers or tissue that are responsible for producing an intended beneficial physiological effect. Teachings of the present invention demonstrate how the disclosed devices may be positioned and used against body surfaces that have arbitrary orientation, such as horizontal and vertical, with respect to the long axis of the component of the device that contains the coil(s). Those teachings also provide methods for treatment of medical conditions that include, but are not limited to, post-operative ileus, neurodegenerative disorders (such as Alzheimer's disease), post-operative cognitive dysfunction (POCD), post-operative delirium (POD), dementia, rheumatoid arthritis, acute and chronic depression, epilepsy, Parkinson's disease, multiple sclerosis (MS), bronchoconstriction associated with asthma, anaphylaxis or COPD, sepsis or septic shock, hypovolemia or hypovolemic shock, orthostatic hypotension, hypertension, urinary incontinence and/or overactive bladder, and sphincter of Oddi dysfunction. However, it should be understood that the disclosed devices and methods may be applied to many other medical conditions, and that their application is not limited to the examples that are given. In other aspects of the invention, the device is used for impedance measurement and imaging, and for repositioning of the coil, monitoring of structural conductivity changes in a patient, and for detecting movement of the coil.

To achieve the above-mentioned objectives, the disclosed magnetic stimulation device uses an efficient method to produce electric fields in tissue noninvasively, namely, to use a toroidal winding around a high magnetic permeability material core, embedded in a conducting medium [Rafael CARBUNARU and Dominique M. Durand. Toroidal coil models for transcutaneous magnetic stimulation of nerves. IEEE Transactions on Biomedical Engineering. 48 (No. 4, April 2001): 434-441]. The conducting medium must have direct contact with skin for current to flow from the coil into the tissue. In essence, the disclosed device produces a transcutaneous current, similar to a transcutaneous electrical nerve stimulation (TENS) device, but with greater depth of penetration and virtually no unpleasant peripheral nerve stimulation. In addition, to generate equivalent electric fields than other PMF devices, toroidal stimulators require only about 0.001-0.1 of the current and produce virtually no heating. It is understood that the magnetic field of a toroidal magnetic stimulator remains essentially within the toroid, and that when referring to this device as a magnetic stimulator, it is in fact the electric fields and/or currents that are induced outside the stimulator that produce an effect in the patient, not the magnetic field.

To the applicant's knowledge, no significant development of toroidal-coil magnetic stimulators has taken place beyond what was reported in the above-mentioned CARBUNARU and Durand publication and the dissertation upon which it was based [Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999. (UMI Microform Number: 9940153, UMI Company, Ann Arbor Mich.)]. Toroidal coils or partial-toroids were mentioned in the following patents or patent applications, but they did not develop the use of a conducting medium in contact with skin: US20080027513, entitled Systems And Methods For Using A Butterfly Coil To Communicate With Or Transfer Power To An Implantable Medical Device, to CARBUNARU; U.S. Pat. No. 7,361,136, entitled Method and apparatus for generating a therapeutic magnetic field, to PARKER; U.S. Pat. No. 6,527,695, entitled Magnetic stimulation coil and circuit design, to DAVEY et al.; U.S. Pat. No. 6,155,966, entitled Apparatus and method for toning tissue with a focused, coherent electromagnetic field, to PARKER; U.S. Pat. No. 4,915,110, entitled Therapeutic electrostatic device, to KITOV; US20070032827, entitled Methods and apparatus for producing therapeutic and diagnostic stimulation, to KATIMS; US20100222629, entitled Method and apparatus for magnetic induction therapy, to BURNETT et al. The latter application to BURNETT et al. only notes that "in the paper titled 'Contactless Nerve Stimulation and Signal Detection by Inductive Transducer' presented at the 1969 Symposium on Application of Magnetism in Bioengineering, Maass et al. disclosed that a nerve threading the lumen of a toroid could be stimulated by a magnetic field."

The lack of development is apparently due to the difficulty of embedding the coil in a practical conducting medium and having that medium be safely in direct contact with human skin. The only reported toroidal-coil magnetic stimulation device used to stimulate human nerves was described in the above-cited dissertation by Rafael Carbunaru FAIERSTEIN, and it embedded the coil in agar. Agar degrades in time and is not ideal to use against skin, presenting difficulties with cleaning it from a patient and within a device. Furthermore, as disclosed there, the toroid needs to be surrounded by conducting medium above, below and around it, making for a relatively bulky device that is difficult to apply to target tissue having small cross sectional area. Furthermore, the device that FAIERSTEIN discloses cannot be applied to the surface of the skin at an arbitrary orientation.

It is therefore a further objective of the present invention to produce a toroidal-coil magnetic stimulation device having a conducting medium that is convenient and practical to use. In particular, the device may be applied to body surfaces having an arbitrary orientation with respect to the long-axis of the component containing the coil. Additional objectives of the disclosed devices are that they be compact and portable, and that they may be adapted for use in nerve and tissue stimulation applications that treat diverse medical conditions, such as post-operative ileus, dysfunction associated with TNF-alpha in Alzheimer's disease, postoperative cognitive dysfunction, rheumatoid arthritis, bronchoconstriction, urinary incontinence and/or overactive bladder, and sphincter of Oddi dysfunction.

The novel systems, devices and methods for treating medical conditions using the disclosed magnetic stimulator are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIGS. 4A-4F illustrate different embodiments of cores according to the present invention, around which magnetic stimulator coil wires may be wound.

FIG. 10 illustrates a method according to the present invention, wherein the disclosed coil is scanned in a raster pattern across a target surface of a patient using a mechanical scanner, in order to acquire an image of the electrical impedance of the coil, including the impedance of underlying electrically conducting bodily tissue.

DETAILED DESCRIPTION OF THE PREFERRED EMBODIMENTS

In the present invention, energy is transmitted non-invasively to a patient. A time-varying magnetic field originating outside of a patient is generated, such that the magnetic field induces an electromagnetic field and/or eddy currents within tissue of the patient. The invention is particularly useful for inducing applied electrical impulses that interact with the signals of one or more nerves, or muscles, to achieve a therapeutic result. In particular, the present disclosure describes devices and methods to treat post-operative ileus, neurodegenerative disorders (such as Alzheimer's disease), post-operative cognitive dysfunction (POCD), post-operative delirium (POD), dementia, rheumatoid arthritis, acute and chronic depression, epilepsy, Parkinson's disease, multiple sclerosis (MS), bronchoconstriction associated with asthma, anaphylaxis or COPD, sepsis or septic shock, hypovolemia or hypovolemic shock, orthostatic hypotension, hypertension, urinary incontinence and/or overactive bladder, and sphincter of Oddi dysfunction or loosening thick mucus in bronchial passages in for example patients suffering from cystic fibrosis.

Figure 1:
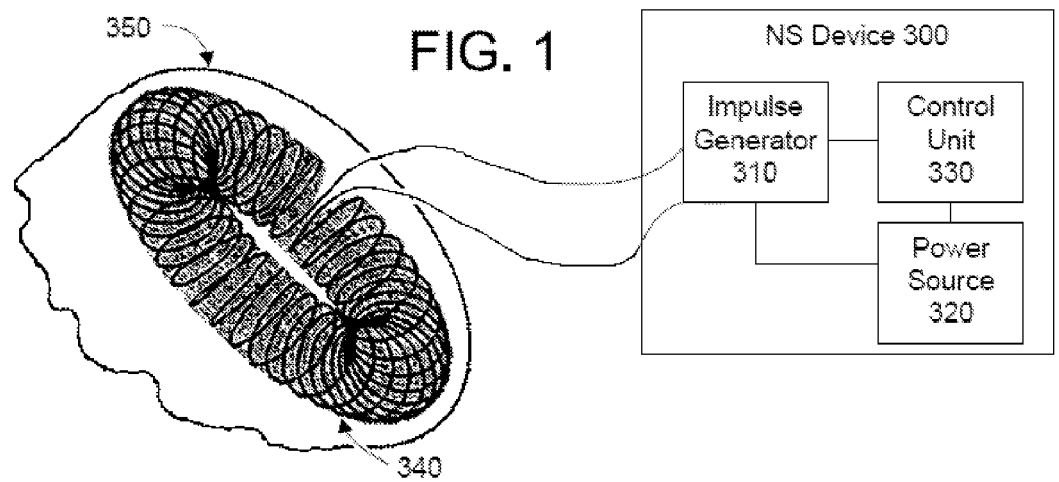
FIG. 1 is a schematic view of an exemplary nerve or tissue modulating device according to the present invention, which supplies controlled pulses of electrical current to a magnetic stimulator coil that is continuously in contact with a volume filled with electrically conducting material.

FIG. 1 is a schematic diagram of a nerve stimulating/modulating device 300 for delivering impulses of energy to nerves for the treatment of medical conditions. As shown, device 300 may include an impulse generator 310; a power source 320 coupled to the impulse generator 310; a control unit 330 in communication with the impulse generator 310 and coupled to the power source 320; and a magnetic stimulator coil 340 coupled via wires to impulse generator coil 310. The stimulator coil 340 is preferably toroidal in shape, due to its winding around a toroid of core material.

Although the magnetic stimulator coil 340 is shown in FIG. 1 to be a single coil, in practice the coil may also comprise two or more distinct coils, each of which is connected in series or in parallel to the impulse generator 310. Thus, the coil 340 shown in FIG. 1 represents all the magnetic stimulator coils of the device collectively. In the preferred embodiment that is disclosed below, coil 340 actually contains two coils that may be connected either in series or in parallel to the impulse generator 310.

The item labeled in FIG. 1 as 350 is a volume, surrounding the coil 340, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 350 corresponds also to sinuousness or curvature on the surface of the body, against which the conducting medium 350 is applied, so as to make the medium and body surface contiguous. As described below in connection with a preferred embodiment, the volume 350 is electrically connected to the patient at a target skin surface in order to significantly reduce the current passed through the coil 340 that is needed to accomplish stimulation of the patient's nerve or tissue. As also described below in connection with a preferred embodiment, the conducting medium in which the coil 340 is embedded need not completely surround the toroid.

The control unit 330 controls the impulse generator 310 to generate a signal for each of the device's magnetic stimulation coils. The signals are selected to be suitable for amelioration of a particular medical condition, when the signals are applied non-invasively to a target nerve or tissue via the magnetic stimulator coil 340. It is noted that nerve stimulating/modulating device 300 may be referred to by its function as a pulse generator. Patent application publications US2005/0075701 and US2005/0075702, both to SHAFER, both of which are incorporated herein by reference, relating to stimulation of neurons of the sympathetic nervous system to attenuate an immune response, contain descriptions of pulse generators that may be applicable to the present invention, when adapted for use with a magnetic stimulator coil. By way of example, a pulse generator 300 is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPUs, computer memories for the storage of executable computer programs (including the system's operating system) and the storage and retrieval of data, disk storage devices, communication devices (such as serial and USB ports) for accepting external signals from the system's keyboard and computer mouse as well as any externally supplied physiological signals, analog-to-digital converters for digitizing externally supplied analog signals, communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals.

Parameters for the nerve or tissue stimulation include power level, frequency and train duration (or pulse number). The stimulation characteristics of each pulse, such as depth of penetration, strength and accuracy, depend on the rise time, peak electrical energy transferred to the coil and the spatial distribution of the electric field. The rise time and peak coil energy are governed by the electrical characteristics of the magnetic stimulator and stimulating coil, whereas the spatial distribution of the induced electric field depends on the coil geometry and the anatomy of the region of induced current flow. In one embodiment of the invention, pulse parameters are set in such as way as to account for the detailed anatomy surrounding the nerve that is being stimulated [Bartosz SAWICKI, Robert Szmurto, Przemystaw Ptonecki, Jacek Starzynski, Stanistaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. A single pulse may be monophasic (no current reversal within the coil), biphasic or polyphasic. For rapid rate stimulators, biphasic systems may be used wherein energy is recovered from each pulse in order to help energize the next. Embodiments of the invention include those that are fixed frequency, where each pulse in a train has the same inter-stimulus interval, and those that have modulated frequency, where the intervals between each pulse in a train can be varied.

Figure 2:
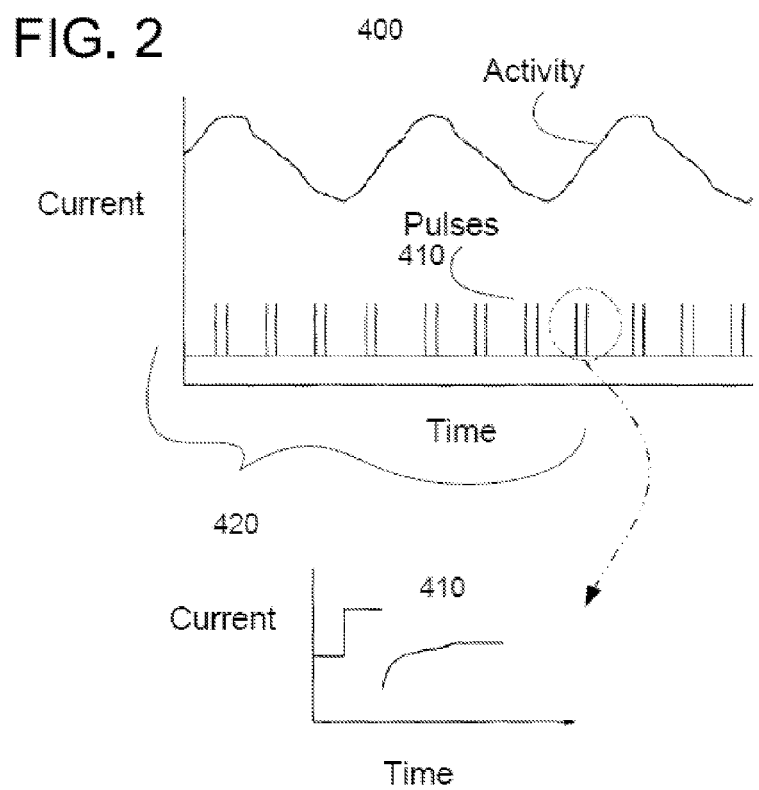
FIG. 2 illustrates an exemplary electrical voltage/current profile for electrical impulses that are applied to a portion or portions of a nerve, in accordance with an embodiment of the present invention.

FIG. 2 illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively induced within the patient by the magnetic stimulator. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the stimulator coils(s) 340 that deliver the stimulating, blocking and/or modulating impulse 410 to the nerve. Nerve stimulating/modulating device 300 may be externally powered and/or recharged may have its own power source 320.

The parameters of the modulation signal 400 are preferably programmable, such as the frequency, amplitude, duty cycle, pulse width, pulse shape, etc. An external communication device may modify the pulse generator programming to improve treatment.

In addition, or as an alternative to the devices to implement the modulation unit for producing the electrical voltage/current profile of the stimulating, blocking and/or modulating impulse to the magnetic stimulator coil, the device disclosed in patent publication No. US2005/0216062 (the entire disclosure of which is incorporated herein by reference) may be employed. U.S. Patent Publication No.: 2005/0216062 discloses a multifunctional electrical stimulation (ES) system adapted to yield output signals for effecting electromagnetic or other forms of electrical stimulation for a broad spectrum of different biological and biomedical applications, including magnetic stimulators, which produce a high intensity magnetic field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 50 Hz, more preferably around 25 Hz. The modulation signal may have a pulse width selected to influence the therapeutic result, such as about 20 microseconds or greater, such as about 20 microseconds to about 1000 microseconds. In certain preferred embodiments, the pulse width is between about 100 to 400 microseconds. For example, the electric field induced by the device within tissue in the vicinity of a nerve is 10 to 600 V/m, preferably around 300 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz.

The preferred embodiment of magnetic stimulator coil 340 comprises a toroidal winding around a core consisting of high-permeability material (e.g., Supermendur), embedded in an electrically conducting medium. Toroidal coils with high permeability cores have been theoretically shown to greatly reduce the currents required for transcranial (TMS) and other forms of magnetic stimulation, but only if the toroids are embedded in a conducting medium and placed against tissue with no air interface. [Rafael CARBUNARU and Dominique M. Durand. Toroidal coil models for transcutaneous magnetic stimulation of nerves. IEEE Transactions on Biomedical Engineering 48 (No. 4, April 2001): 434-441; Rafael Carbunaru FAIERSTEIN, Coil Designs for Localized and Efficient Magnetic Stimulation of the Nervous System. Ph. D. Dissertation, Department of Biomedical Engineering, Case Western Reserve, May, 1999, page 117 (UMI Microform Number: 9940153, UMI Company, Ann Arbor Mich.)].

In order to explain some of the novelty of the presently disclosed invention as compared with the device described in the above-mentioned Carbunaru and Durand publication, as well as in the FAIERSTEIN dissertation upon which the publication was based, it is useful to first summarize the relevant physics of electric fields and currents that are induced by time-varying magnetic fields, as produced by current—carrying coils [Richard P. FEYNMAN, Robert B. Leighton, and Matthew Sands. The Feynman Lectures on Physics. Volume II. Addison-Wesley Publ. Co. (Reading Mass., 1964), page 15-15; K. P. ESSELLE and M. A. Stuchly, Neural stimulation with magnetic fields: Analysis of induced electric fields, IEEE Trans. Biomed. Eng., 39 (July 1992), pp. 693-700; R. BOWTELL and R. M. Bowley. Analytic Calculations of the E-Fields Induced by Time-Varying Magnetic Fields Generated by Cylindrical Gradient Coils. Magnetic Resonance in Medicine 44:782-790 (2000); Feng LIU, Huawei Zhao, and Stuart Crozier. On the Induced Electric Field Gradients in the Human Body for Magnetic Stimulation by Gradient Coils in MRI, IEEE Transactions on Biomedical Engineering 50: (No. 7, July 2003) pp. 804-815].

The magnetic field B may be represented as the curl of a vector potential A, where B and A are functions of position and time: $B = \nabla \times A$ The electric field E, which is also a function of position and time, consists of two parts, E1 and E2: $E = E_1 + E_2$. For a current-carrying coil, E1 is obtained from the vector potential A by:

$$E_1 = -\frac{\partial A}{\partial t} = -\int \frac{1}{4\pi} \frac{\partial (\mu I)}{\partial t} \frac{dt}{r}$$

where μ is the permeability, I is the current flowing in the coil, dl is an oriented differential element of the coil, r is the distance between dl and the point at which the electric field E is measured, and the integral is performed around all the differential elements dl of the coil.

E2 is obtained from the gradient of a scalar potential Φ: $E_2=-\nabla\Phi$. The scalar potential arises because conductivity changes along the path of a current, particularly the abrupt change of conductivity at an air/conductor interface, causes electric charges to separate and accumulate on the surface of the interface, with the amplitude and sign of the charges changing as a function of surface position. Thus, no conduction current can flow across an air/conductor interface, so according to the interfacial boundary conditions, the component of any induced current normal to the interface must be zero. The existence of a scalar potential accounts for these effects.

The electrical current density J, which is also a function of position and time, consists of two parts: $J=J1+J2$, corresponding to the two parts of E: $J_1=\sigma E_1$ and $J_2=\sigma E_2$, where the conductivity σ is generally a tensor and a function of position. If the current flows in material that is essentially unpolarizable (i.e., is presumed not to be a dielectric), any displacement current may be ignored, so the current would satisfy Ampere's law:

$$\nabla \times \frac{B}{\mu} = J.$$

Because the divergence of the curl is zero, $\nabla \cdot J=0$. One may substitute J1 and J2 into that equation to obtain: $\nabla \cdot (\sigma(E_1 - \nabla\Phi))=0$. The latter equation has been solved numerically for special cases to estimate the currents that are induced by a magnetic field that is inserted into the body [W. WANG, S. R. Eisenberg, A three-dimensional finite element method for computing magnetically induced currents in tissues. IEEE Transactions on Magnetics. 30 (6 Nov. 1994): 5015-5023; Bartosz SAWICKI, Robert Szmurto, Przemystaw Ptonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. If the conductivity of material in the device (or patient) is itself selected to be a function of the electric field, then the equation becomes non-linear, which could exhibit multiple solutions, frequency multiplication, and other such non-linear behavior.

If the displacement current cannot be ignored, the displacement appears as a term involving the time-derivative of the electric field in the more general expression: $\nabla \cdot (\partial(\in E)/\partial t + \sigma(E_1 - \nabla\Phi))=0$, where $\in$ is the permittivity, which is a function of position and is generally a tensor. As a consequence of such a term, the waveform of the electric field at any point will generally be altered relative to the waveform of the current I(t) that is passed through the coils. Furthermore, if the permittivity of a material in the device is itself selected to be a function of the electric field, then the equation becomes non-linear, which could exhibit multiple solutions, frequency multiplication, and other such non-linear behavior.

The above-mentioned publication by CARBUNARU and Durand, as well as the FAIERSTEIN dissertation upon which the publication was based, are heretofore unique in that they describe a magnetic stimulation device that does not create a magnetic field within the tissues that the device is intended to stimulate. Their device instead confines the magnetic field to a toroid, which is the only coil geometry known to create a magnetic field that is completely limited to part of space. With such a device, the electric field alone penetrates the patient to stimulate nerves or tissue, which they calculate using device-specific equations for the fields E1 and E2 that were defined above. Unlike conventional magnetic stimulation devices, their device's electric field orientation is not limited to fields at the skin that are parallel to the skin surface, due to the presence of conducting material that extends from the skin to (and beyond) the stimulator's coil. The boundary conditions giving rise to E2 were those of an infinite half-space. Thus, their toroidal coil was immersed in a homogeneous continuous conducting material that had an air/conductor interface along an infinite plane parallel to the toroid, located at a variable distance from the toroid, and the toroid and conducting material were in contact with a patient's skin.

In their investigations, Carbunaru and Durand varied E1 by only changing the coil geometry (integral over dl) as follows. They investigated winding the coil around different core geometries (round, quarter circle, square) and changed the radius and thickness of the core. They also varied E2 by varying the thickness of the conducting layer in which the toroid was immersed, thereby changing boundary conditions only in that manner. Although Carbunaru and Durand demonstrated that it is possible to electrically stimulate a patient transcutaneously with such a device, they made no attempt to develop the device in such a way as to generally shape the electric field to stimulate the nerve. In particular, the electric fields that may be produced by their device are limited to those that are radially symmetric at any given depth of stimulation into the patient (i.e, z and ρ are used to specify location of the field, not x, y, and z). This is a significant limitation, and it results in a deficiency that was noted in FIG. 6 of their publication: "at large depths of stimulation, the threshold current [in the device's coil] for long axons is larger than the saturation current of the coil. Stimulation of those axons is only possible at low threshold points such as bending sites or tissue conductivity inhomogeneities". Thus, for their device, varying the parameters that they considered, in order to increase the electric field or its gradient in the vicinity of a nerve, may come at the expense of limiting the field's physiological effectiveness, such that the spatial extent of the field of stimulation may be insufficient to modulate the target nerve's function. Yet, such long axons are precisely what we may wish to stimulate in therapeutic interventions, such as the ones disclosed herein.

Accordingly, it is an objective of the present invention to shape an elongated electric field of effect that can be oriented parallel to such a long nerve. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which induced current flow is restricted. Shaping of the electric field refers both to the circumscribing of regions within which there is a significant electric field and to configuring the directions of the electric field within those regions.

Thus, the present invention differs from the device disclosed by CARBUNARU and Durand by deliberately shaping an electric field that is used to transcutaneously stimulate the patient. Our invention does so by configuring elements that are present within the equations that were summarized above, comprising (but not limited to) the following exemplary configurations that may be used alone or in combination.

First, the contours of the coil differential elements dl that are integrated in the above equation for E1 are shaped into a geometry other than a single planar toroid. For example, two separate toroidal coils are used so that E1 becomes the sum of two integrals, or the shape of a single toroid is twisted to resemble a figure-of-8 rather than a planar toroid.

Second, the value of the current I in the above equation for E1 is manipulated to shape the electric field. For example, if the device contains two toroidal coils, the current in one toroid may be the negative of the current in the other toroid. As another example, the magnitude of the current in a left toroidal coil may be varied relative to the magnitude of the current in a right toroidal coil, so that the location of their superimposed induced electric fields may be correspondingly moved (focused) in the left or right directions.

Third, the scalar potential $\Phi$ in the above equation for E2 is manipulated to shape the electric field. For example, this is accomplished by changing the boundaries of conductor/air (or non-conductor) interfaces, thereby creating different boundary conditions. Whereas the toroid in the CARBUNARU and Durand publication was immersed in a homogeneous conducting half-space, this is not necessarily the case for our invention. Although our invention will generally have some continuously conducting path between the device's coil and the patient's skin, the conducting medium need not totally immerse the coil, and there may be insulating voids within the conducting medium. For example, if the device contains two toroids, conducting material may connect each of the toroids individually to the patient's skin, but there may be an insulating gap (from air or some other insulator) between the surfaces at which conducting material connected to the individual toroids contact the patient. Furthermore, the area of the conducting material that contacts the skin may be made variable, by using an aperture adjusting mechanism such as an iris diaphragm. As another example, if the coil is wound around core material that is laminated, with the core in contact with the device's electrically conducting material, then the lamination may be extended into the conducting material in such a way as to direct the induced electrical current between the laminations and towards the surface of the patient's skin. As another example, the conducting material may pass through apertures in an insulated mesh before contacting the patient's skin, creating thereby an array of electric field maxima.

Fourth, the conductivity $\sigma$ (in the equations $J=\sigma E_1$ and $J_2=\sigma E_2$) may be varied spatially within the device by using two or more different conducting materials that are in contact with one another, for given boundary conditions. The conductivity may also be varied by constructing some conducting material from a semiconductor, which allows for adjustment of the conductivity in space and in time by exposure of the semiconductor to agents to which they are sensitive, such as electric fields, light at particular wavelengths, temperature, or some other environmental variable over which the user of the device has control. For the special case in which the semiconductor's conductivity may be made to approach zero, that would approximate the imposition of an interfacial boundary condition as described in the previous paragraph. As another example, the conducting material of the device may be selected to have a three-dimensional conductivity structure that approximates that of the conducting tissue under the patient's skin, but oriented in the opposite and/or mirror image directions, in such a way that the conductivity is symmetrical on either side of the patient's skin. Such an arrangement will allow for essentially symmetrical electrical stimulation of the patient's tissue and the conducting material within the device.

Fifth, a dialectric material having a high permittivity $\in$, such as Mylar, neoprene, titanium dioxide, or strontium titanate, may be used in the device, for example, in order to permit capacitive electrical coupling to the patient's skin.

Sixth, the present invention is more general than the device described in the above-mentioned publication of CARBUNARU and Durand in that, although the magnetic field produced by the present invention does not effectively penetrate the patient's tissue, that feature need not be due to the use of a toroidal coil. The magnetic field will not effectively penetrate the patient's tissue if the field's de minimis existence within the patient would produce no significant physiological effect. For example, it would not produce a significant physiological effect if the magnitude of the magnetic field were of the same order of magnitude as the earth's magnetic field. The magnetic field of our disclosed device may be produced by a coil other than a toroid, wherein the magnetic field outside the coil falls rapidly as a function of distance from the coil. For example, the coil may be a solenoid that has an approximately centrally-confined magnetic field as the density of coil turns and the length of the solenoid increase. As another example, the coil may be a partial toroid, which would also have a magnetic field that approximates that of a complete toroid as the gap within the partial-toroid decreases to zero. As another example, even if one is attempting to construct a complete toroidal winding, the presence of lead wires and imperfections of the winding may cause the device in practice to deviate from the ideal toroid. Such non-toroidal windings may be used in the present invention if they are backed away and/or oriented relative to the patient's skin in such a way that the magnetic field that is produced by the device does not effectively penetrate the patient's tissue. Alternatively, magnetic shielding, such as mumetal, supermalloy, supermumetal, nilomag, sanbold, molybdenum permalloy, Sendust, M-1040, Hipernom and HyMu-80, may be interposed between the patient and coil of the device in such a way that the magnetic field that is produced by the device does not effectively penetrate the patient's tissue.

In the dissertation cited above, Carbunaru-FAIERSTEIN made no attempt to use conducting material other than agar in a KCI solution, and he made no attempt to devise a device that could be conveniently and safely applied to a patient's skin, at an arbitrary angle without the conducting material spilling out of its container. It is therefore an objective of the present invention to disclose conducting material that can be used not only to adapt the conductivity $\sigma$ and select boundary conditions, thereby shaping the electric fields and currents as described above, but also to create devices that can be applied practically to any surface of the body. The volume of the container containing electrically conducting medium is labeled in FIG. 1 as 350. Use of the container of conducting medium 350 allows one to generate (induce) electric fields in tissue (and electric field gradients and electric currents) that are equivalent to those generated using current magnetic stimulation devices, but with about 0.0001 to 0.01 of the current conventionally applied to a magnetic stimulation coil. This allows for minimal heating and deeper tissue stimulation. However, application of the conducting medium to the surface of the patient is difficult to perform in practice because the tissue contours (head for TMS, arms, legs, neck, etc. for peripheral nerve stimulation) are not planar. To solve this problem, in the preferred embodiment of the present invention, the toroidal coil is embedded in a structure which is filled with a conducting medium having a much higher conductivity as muscle tissue, as now described. In the preferred embodiment, the conducting medium will have a conductivity that is equivalent to saline or up to 10 times the conductivity of saline.

In one embodiment of the invention, the container contains holes or apertures so that the conducting material (e.g., a conducting gas, liquid or gel) can make physical contact with the patient's skin through the holes. For example, the conducting medium 350 may comprise a chamber surrounding the coil, filled with a conductive gel that has the approximate viscosity and mechanical consistency of gel deodorant (e.g., Right Guard Clear Gel from Dial Corporation, 15501 N. Dial Boulevard, Scottsdale Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is preferably a conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue. A device such as that disclosed in U.S. Pat. No. 7,591,776, entitled Magnetic stimulators and stimulating coils, to PHILLIPS et al. may conform the coil itself to the contours of the body, but in the preferred embodiment, such a curved coil is also enclosed by a container that is filled with a conducting medium that deforms to be contiguous with the skin.

Agar can also be used as part of the conducting medium, but it is not preferred, because agar degrades in time, is not ideal to use against skin, and presents difficulties with cleaning the patient and stimulator coil. Use of agar in a 4M KCl solution as a conducting medium was mentioned in the above-cited dissertation: Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor Mich.). However, that publication makes no mention or suggestion of placing the agar in a conducting elastomeric balloon, or other deformable container so as to allow the conducting medium to conform to the generally non-planar contours of a patient's skin having an arbitrary orientation. In fact, that publication describes the coil as being submerged in a container filled with an electrically conducting solution. If the coil and container were placed on a body surface that was oriented in the vertical direction, then the conducting solution would spill out, making it impossible to stimulate the body surface in that orientation. In contrast, the present invention is able to stimulate body surfaces having arbitrary orientation. Examples making use of the present device show the body surface as having many different orientations (FIGS. 6, 8, 9, and 10) that are incompatible with the disclosure in the above-cited dissertation.

That dissertation also makes no mention of a dispensing method whereby the agar would be made contiguous with the patient's skin. A layer of electrolytic gel is said to have been applied between the skin and coil, but the configuration was not described clearly in the publication. In particular, no mention is made of the electrolytic gel being in contact with the agar.

Rather than using agar as the conducting medium, the coil can instead be embedded in a conducting solution such as 0.9-10% NaCl, contacting an electrically conducting interface to the human tissue. Such an interface is used as it allows current to flow from the coil into the tissue and supports the medium-surrounded toroid so that it can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J Martens. Conducting polymer-hydrogels for medical electrode applications. Sci. Technol. Adv. Mater. 11 (2010) 014107 (13pp)]. For example it may be the following hypoallergenic, bacteriostatic electrode gel: SIGNAGEL Electrode Gel from Parker Laboratories, Inc., 286 Eldridge Rd., Fairfield N.J. 07004.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the toroid and the solution it is embedded in from the tissue, yet allow current to pass.

The preferred embodiment of the magnetic stimulator coil 340 in FIG. 1 reduces the volume of conducting material that must surround a toroidal coil, by using two toroids, side-by-side, and passing electrical current through the two toroidal coils in opposite directions. In this configuration, the induced current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is particularly advantageous for exciting long, straight axons such as the vagus nerve and certain peripheral nerves.

This preferred embodiment of the invention is shown in FIG. 3. FIGS. 3A and 3B respectively provide top and bottom views of the outer surface of the toroidal magnetic stimulator 30. FIGS. 3C and 3C respectively provide top and bottom views of the toroidal magnetic stimulator 30, after sectioning along its long axis to reveal the inside of the stimulator.

FIGS. 3A-3D all show a mesh 31 with openings that permit a conducting gel to pass from the inside of the stimulator to the surface of the patient's skin at the location of nerve or tissue stimulation. Thus, the mesh with openings 31 is the part of the stimulator that is applied to the skin of the patient.

Figure 3A:
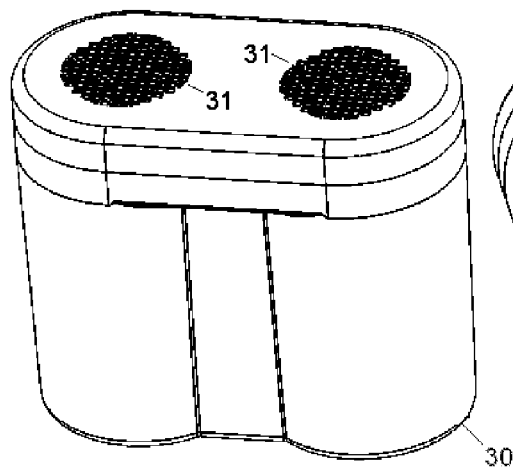
FIGS. 3A-3D illustrate a dual-toroid magnetic stimulator coil according to an embodiment of the present invention, which is shown to be situated within a housing that contains electrically conducting material.
Figure 3B:
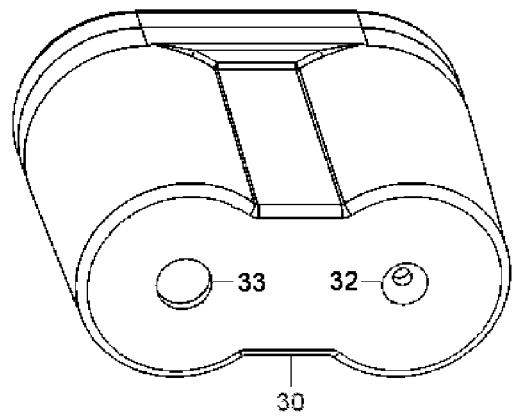
Figure 3C:
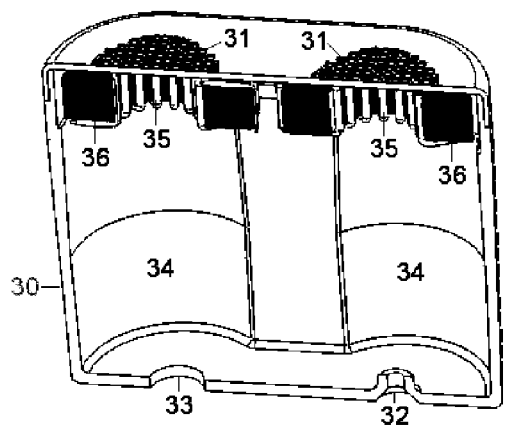
Figure 3D:
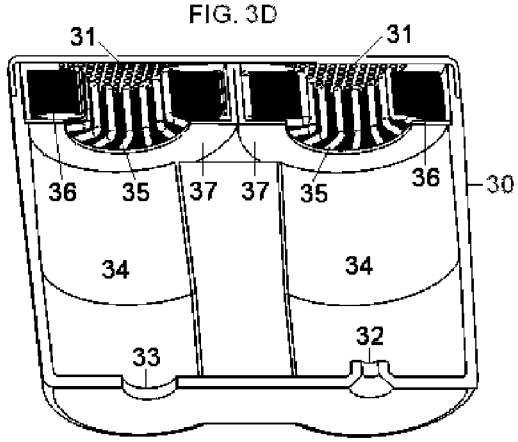

FIGS. 3B-3D show openings at the opposite end of the stimulator 30. One of the openings is an electronics port 32 through which wires pass from the stimulator coil(s) to the impulse generator (310 in FIG. 1). The second opening is a conducting gel port 33 through which conducting gel may be introduced into the stimulator 30 and through which a screw-driven piston arm may be introduced to dispense conducting gel through the mesh 31. The gel itself will be contained within cylindrical-shaped but interconnected conducting medium chambers 34 that are shown in FIGS. 3C and 3D.

In the prior art device, the depth of the conducting medium chambers 34, which is approximately the height of the long axis of the stimulator, affects the magnitude of the electric fields and currents that are induced by the device [Rafael CARBUNARU and Dominique M. Durand. Toroidal coil models for transcutaneous magnetic stimulation of nerves. IEEE Transactions on Biomedical Engineering. 48 (No. 4, April 2001): 434-441]. The present invention, however, utilizes a conductive medium that has a much higher conductivity than the patient's tissue, which makes the device of the present invention significantly more efficient than the device described in the Carbunaru article. Therefore, the depth of the conducting medium chambers 34 is not critical to the performance of the device and not critical to enabling the electric field or current to be passed through the patient's skin to the target region.

FIGS. 3C and 3D also show the coils of wire 35 that are wound around toroidal cores 36, consisting of high-permeability material (e.g., Supermendur). Lead wires (not shown) for the coils 35 pass from the stimulator coil(s) to the impulse generator (310 in FIG. 1) via the electronics port 32. Different circuit configurations are contemplated. If separate lead wires for each of the coils 35 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As seen in FIGS. 3C and 3D, the coils 35 and cores 36 around which they are wound are mounted as close as practical to the corresponding mesh 31 with openings through which conducting gel passes to the surface of the patient's skin. As seen in FIG. 3D, each coil and the core around which it is wound is mounted in its own housing 37, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance.

The embodiment shown in FIG. 3 contains two toroids, in which the outer surface of the toroids are planar, the toroids lie side-by-side, and the corresponding outer surfaces for both toroids lie essentially in the same plane. Many different embodiments are also contemplated, each of which may be better suited to the stimulation of particular nerves or tissues. Examples of such alternate embodiments are illustrated in FIG. 4, showing the geometry of the toroidal core material around which coils of wire (not shown) would be wound. The darkened faces of the figures shown there indicate the faces that would be oriented towards the patient's skin. Instead of placing the toroids side-by-side as in FIG. 3, a pair of toroids may be placed concentrically as shown in FIG. 4A. Instead of using two toroids, any number could be used, as illustrated by FIG. 4B that shows four concentrically positioned toroids. Individual planar toroids need not all lie in the same plane, as shown in FIG. 4C. In fact, the toroids themselves need not have a planar structure, as illustrated in FIGS. 4D and 4E. Furthermore, the toroids need not have a round structure or a structure comprising arcs, as illustrated in FIG. 4F, which shows a pair of concentrically positioned square toroids. The examples shown here have toroids that are rectangular or square when sectioned perpendicular to their perimeters. In other embodiments, the sectioned toroid could have any other closed geometry, such as a circle or an ellipse or a geometry that changes from one part of the toroid to another.

Thus, the geometrical configuration of the disclosed device is general. For example, it may comprise a plurality of toroids. It may comprise two toroids wherein one toroid lies within the aperture of the second toroid. A surface having a minimum area that fills an aperture of a toroid need not lie within a plane. The projection of the volume of a toroidal core onto a plane need not produce a circular shape around any perimeter of any such projection. For a plurality of toroids, a plane having a greatest area of intersection through one toroid among the plurality may, but need not, be parallel to a plane having a greatest area of intersection through some second toroid among the plurality.

The design and methods of use of impulse generators, control units, and stimulator coils for magnetic stimulators are informed by the designs and methods of use of impulse generators, control units, and electrodes (with leads) for comparable completely electrical nerve stimulators, but design and methods of use of the magnetic stimulators must take into account many special considerations, making it generally not straightforward to transfer knowledge of completely electrical stimulation methods to magnetic stimulation methods. Such considerations include determining the anatomical location of the stimulation and determining the appropriate pulse configuration [OLNEY R K, So Y T, Goodin D S, Aminoff M J. A comparison of magnetic and electric stimulation of peripheral nerves. Muscle Nerve 1990:13:957-963; J. NILSSON, M. Panizza, B. J. Roth et al. Determining the site of stimulation during magnetic stimulation of the peripheral nerve, Electroencephalographs and clinical neurophysiology. vol 85, pp. 253-264, 1992; Nafia AL-MUTAWALY, Hubert de Bruin, and Gary Hasey. The Effects of Pulse Configuration on Magnetic Stimulation. Journal of Clinical Neurophysiology 20(5):361-370, 2003].

Figure 5:
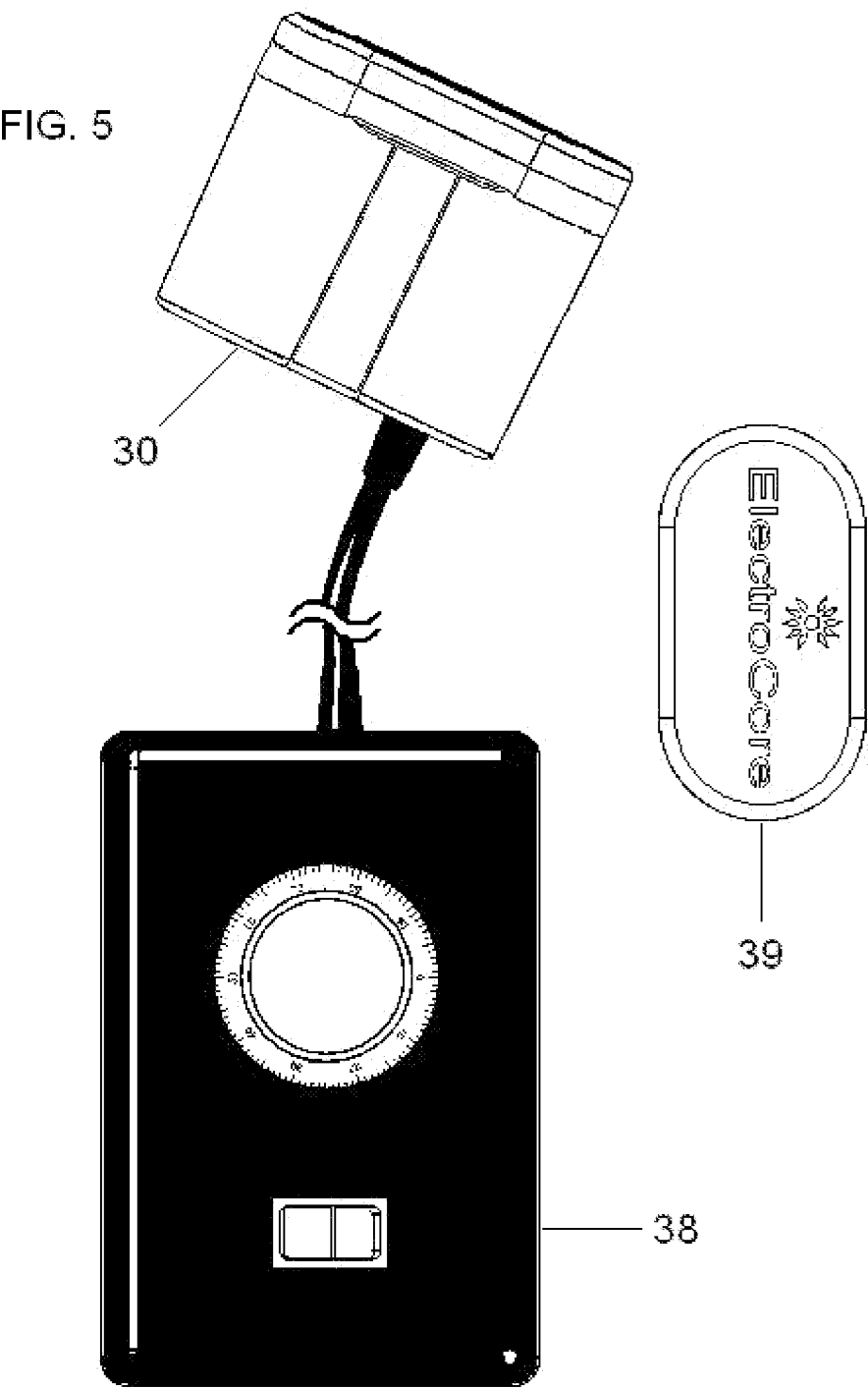
FIG. 5 illustrates the housing and cap of the dual-toroid magnetic stimulator coils of FIGS. 3A-3D, attached via cable to a box containing the device's impulse generator, control unit, and power source.

In the preferred embodiment of the invention, electronic components of the stimulator (impulse generator, control unit, and power source) are compact, portable, and simple to operate. The preferred simplicity is illustrated in FIG. 5, which shows the stimulator coil housing 30 (illustrated in more detail as 30 in FIG. 3), which is connected by electrical cable to a circuit control box 38. As shown in FIG. 5, the circuit control box 38 will generally require only an on/off switch and a power controller, provided that the parameters of stimulation described in connection with FIG. 2 have already been programmed for the particular application of the device. For such a portable device, power is provided by batteries, e.g., a 9 volt battery or two to six 1.5V AA batteries. A covering cap 39 is also provided to fit snugly over the mesh (31 in FIG. 3) of the stimulator coil housing 30, in order to keep the housing's conducting medium from leaking or drying when the device is not in use.

In the preferred embodiment for a generic therapeutic application, the currents passing through the coils of the magnetic stimulator will saturate the core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses. The burst repeats at 1 Hz to 5000 Hz, preferably at 15-50 Hz. The pulses have duration of 20 to 1000 microseconds, preferably 200 microseconds and there may be 1 to 20 pulses per burst. Other waveforms described above in connection with FIG. 2 are also generated, depending on the nerve or tissue stimulation application.

Examples in the remaining disclosure will be directed to use of the disclosed toroidal magnetic stimulation device for treatment of specific medical conditions. These applications involve stimulating a patient in and around the patient's neck, abdomen, ankle, and head. However, it will be appreciated that the systems and methods of the present invention can be applied equally well to other tissues and nerves of the body, including but not limited to parasympathetic nerves, sympathetic nerves, spinal or cranial nerves, and brain tissue. In addition, the present invention can be used to directly or indirectly stimulate or otherwise modulate nerves that innervate smooth or skeletal muscle, endocrine glands, and organs of the digestive system.

In some preferred embodiments of methods that make use of the disclosed toroidal-coil magnetic stimulation device, selected nerve fibers are stimulated. These include stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is ordinarily selected for stimulation because stimulation of the right vagus nerve may produce undesired effects on the heart.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6:
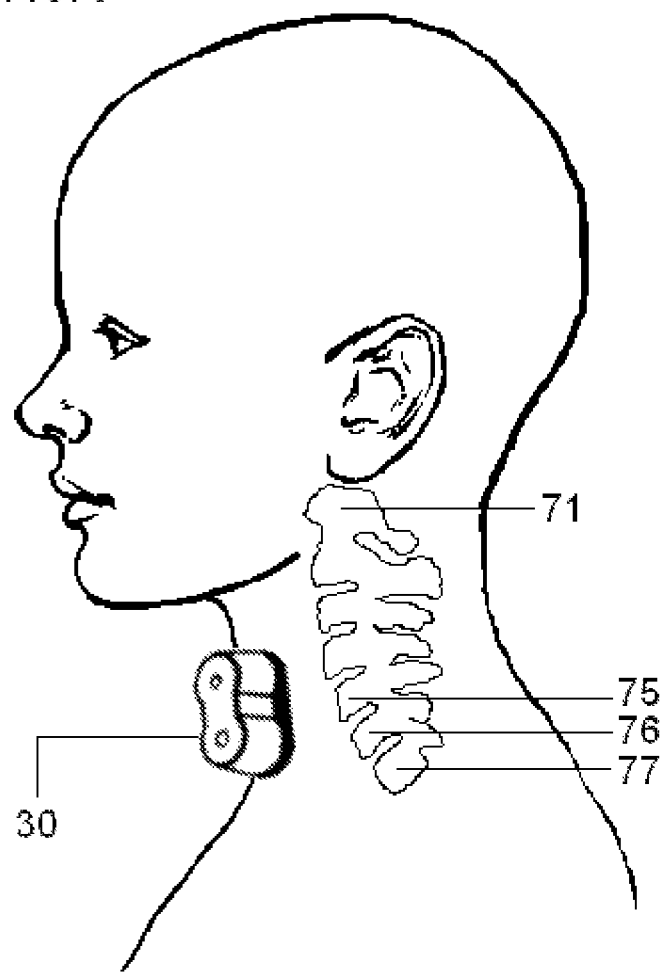
FIG. 6 illustrates the approximate position of the housing of the magnetic stimulator coil according to one embodiment of the present invention, when the coil is used to stimulate the vagus nerve in the neck of a patient.

FIG. 6 illustrates use of the device shown in FIG. 3 and FIG. 5 to stimulate the vagus nerve at that location in the neck, in which the stimulator device 30 is applied to the target location on the patient's neck as described above. For reference, locations of the following vertebrae are also shown: first cervical vertebra 71, the fifth cervical vertebra 75, the sixth cervical vertebra 76, and the seventh cervical vertebra 77.

Figure 7:
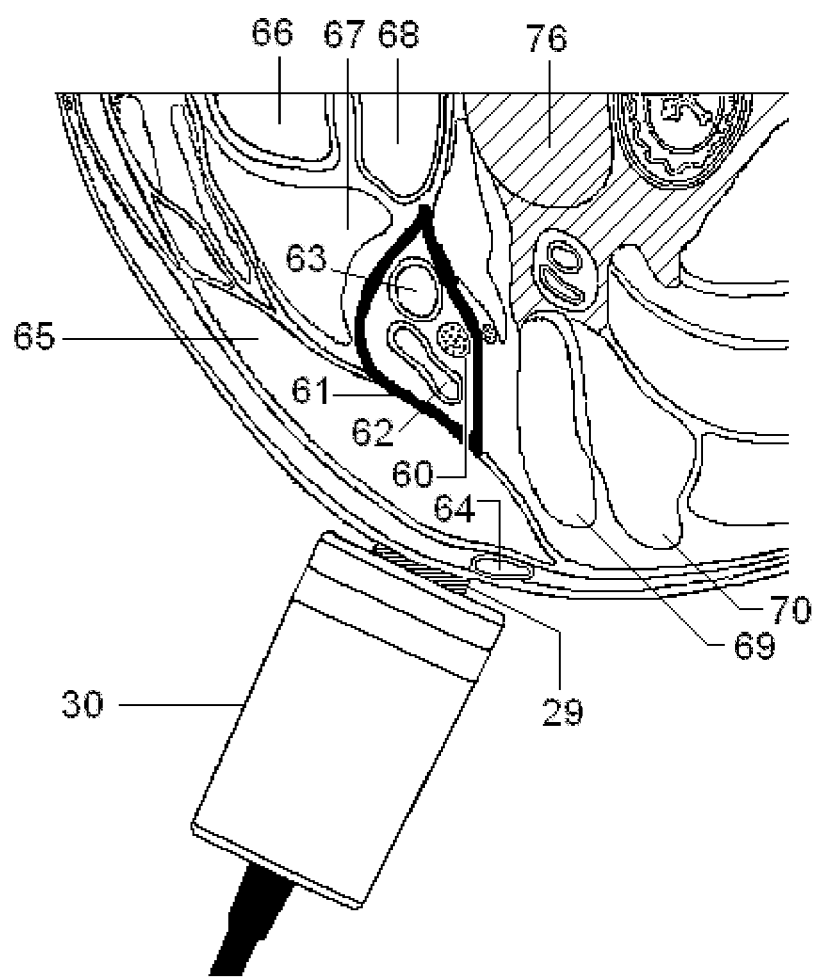
FIG. 7 illustrates the housing of the magnetic stimulator coil according to one embodiment of the present invention, as the coil is positioned to stimulate the vagus nerve in a patient's neck via electrically conducting gel (or some other conducting material), which is applied to the surface of the neck in the vicinity of the identified anatomical structures.

FIG. 7 provides a more detailed view of use of the toroidal magnetic stimulator device, when positioned to stimulate the vagus nerve at the neck location that is indicated in FIG. 6.

As shown, the toroidal magnetic stimulator 30 touches the neck indirectly, by making electrical contact through conducting gel 29 (or other conducting material) that is dispensed through mesh openings of the stimulator (identified as 31 in FIG. 3). It is understood that the device 30 is connected via wires or cables (not shown) to an impulse generator 310 as in FIG. 1, although it is also possible that device 30 may be battery operated and/or wirelessly connected to generator 310. The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

Magnetic stimulation has been used by several investigators to non-invasively stimulate the vagus nerve, in the neck and at other locations. In a series of articles beginning in 1992, Aziz and colleagues describe using non-invasive magnetic stimulation to electrically stimulate the vagus nerve in the neck. [Q. AZIZ et al. Magnetic Stimulation of Efferent Neural Pathways to the Human Oesophagus. Gut 33: S53-S70 (Poster Session F218) (1992); AZIZ, Q., J. C. Rothwell, J. Barlow, A. Hobson, S. Alani, J. Bancewicz, and D. G. Thompson. Esophageal myoelectric responses to magnetic stimulation of the human cortex and the extracranial vagus nerve. Am. J. Physiol. 267 (Gastrointest. Liver Physiol. 30): G827-G835, 1994; Shaheen HAMDY, Qasim Aziz, John C. Rothwell, Anthony Hobson, Josephine Barlow, and David G. Thompson. Cranial nerve modulation of human cortical swallowing motor pathways. Am. J. Physiol. 272 (Gastrointest. Liver Physiol. 35): G802-G808, 1997; Shaheen HAMDY, John C. Rothwell, Qasim Aziz, Krishna D. Singh, and David G. Thompson. Long-term reorganization of human motor cortex driven by short-term sensory stimulation. Nature Neuroscience 1 (issue 1, May 1998):64-68.] SIMS and colleagues stimulated the vagus nerve at and near the mastoid tip. [H. Steven SIMS, Toshiyuki Yamashita, Karen Rhew, and Christy L. Ludlow. Assessing the clinical utility of the magnetic stimulator for measuring response latencies in the laryngeal muscles. Otolaryngol Head Neck Surg 1996; 114:761-7]. KHEDR and colleagues also used a magnetic stimulator to stimulate the vagus nerve at the tip of the mastoid bone [E. M. KHEDR and E-E. M. Aref Electrophysiological study of vocal-fold mobility disorders using a magnetic stimulator. European Journal of Neurology 2002, 9: 259-267; KHEDR, E. M., Abo-Elfetoh, N., Ahmed, M. A., Kamel, N. F., Farook, M., El Karn, M. F. Dysphagia and hemispheric stroke: A transcranial magnetic study. Neurophysiologie Clinique/Clinical Neurophysiology (2008) 38, 235-242)]. SHAFIK stimulated the vagus nerve in the neck, placing the magnetic stimulator on the neck between the sternomastoid muscle and the trachea. [A. SHAFIK. Functional magnetic stimulation of the vagus nerve enhances colonic transit time in healthy volunteers. Tech Coloproctol (1999) 3:123-12]. Among these investigations, the one by SHAFIK stimulated the vagus nerve for the longest period of time. He stimulated at 175 joules per pulse, 40 Hz frequency, 10 seconds on, 10 seconds off for 20 minutes duration and followed by 60 minutes of rest, and this sequence was performed for 5 cycles in each subject.

The vagus is not the only nerve that may be stimulated non-invasively in the neck using magnetic stimulation. For example, the phrenic nerve has also been magnetically stimulated. [SIMILOWSKI, T., B. Fleury, S. Launois, H. P. Cathala, P. Bouche, and J. P. Derenne. Cervical magnetic stimulation: a new painless method for bilateral phrenic nerve stimulation in conscious humans. J. Appl. Physiol. 67(4): 1311-1318, 1989; Gerrard F. RAFFERTY, Anne Greenough, Terezia Manczur, Michael I. Polkey, M. Lou Harris, Nigel D. Heaton, Mohamed Rela, and John Moxham. Magnetic phrenic nerve stimulation to assess diaphragm function in children following liver transplantation. Pediatr Crit Care Med 2001, 2:122-126; W. D-C. MAN, J. Moxham, and M. I. Polkey. Magnetic stimulation for the measurement of respiratory and skeletal muscle function. Eur Respir J 2004; 24: 846-860]. If one intends to stimulate only the vagus nerve, careful positioning of the stimulator coil should be undertaken in order to avoid co-stimulation of the phrenic nerve, or the magnetic stimulation waveform may be designed to minimize the effect of any co-stimulation of the vagus and phrenic nerves [patent application JP2008/081479A, entitled Vagus nerve stimulation system, to YOSHIHOTO].

If it is desired to maintain a constant intensity of stimulation in the vicinity of the vagus nerve (or any other nerve or tissue that is being stimulated), methods may also be employed to modulate the power of the stimulator in order to compensate for patient motion or other mechanisms that would otherwise give rise to variability in the intensity of stimulation. In the case of stimulation of the vagus nerve, such variability may be attributable to the patient's breathing, which may involve contraction and associated change in geometry of the sternocleidomastoid muscle that is situated close to the vagus nerve (identified as 65 in FIG. 7). Methods for compensating for motion and other confounding factors were disclosed by the present applicant in co-pending U.S. patent application Ser. No. 12/859,568 filed Aug. 19, 2010 entitled Non-Invasive Treatment of Bronchial Constriction, to SIMON, which is hereby incorporated by reference. In the present application, an additional compensation method is disclosed below. In brief, the electrical impedance of the magnetic stimulator coil is monitored to ascertain whether that impedance is fluctuating as a function of the phase of respiration (or other contributing variable such as drift). If such fluctuation is found, the power to coil(s) of the magnetic stimulator may be modulated as a function of the phase of respiration or other contributing factor, in order to compensate.

Several examples follow, exemplifying therapies involving stimulation of the vagus nerve in the neck using the disclosed magnetic stimulation device. However, it is understood that stimulation of the vagus nerve could also be performed at locations other than the neck [Polak T, Markulin F, Ehlis A C, Langer J B, Ringel T M, Fallgatter A J. Far field potentials from brain stem after transcutaneous vagus nerve stimulation: optimization of stimulation and recording parameters. J Neural Transm. 2009 October; 116(10):1237-42]. Examples of vagus nerve stimulation are for the treatment of post-operative ileus, for treatment of dysfunction associated with TNF-alpha in Alzheimer's disease, for treatment of postoperative cognitive dysfunction, and for treatment of rheumatoid arthritis. Although the mechanisms and details of the treatment of these diseases are different, one aspect that they have in common is that they may be at least partially related to inflammation that may be controlled by stimulation of the vagus nerve [JOHNSTON G R, Webster NR. Cytokines and the immunomodulatory function of the vagus nerve. Br J Anaesth (2009) 102:453-62; GROVES D A, Brown V J. Vagal nerve stimulation: a review of its applications and potential mechanisms that mediate its clinical effects. Neurosci Biobehav Rev (2005) 29:493-500; GUYON A, Massa F, Rovère C, Nahon J L. How cytokines can influence the brain: a role for chemokines? J Neuroimmunol 2008; 198:46-55.]. Those examples are followed by an example of stimulation of the vagus nerve in the neck using the disclosed device, in order to treat bronchoconstriction. That is followed by examples of therapies for disorders involving stimulation using the device disclosed here, in which the disorders do not necessarily involve stimulation of the vagus nerve.

Postoperative ileus is a temporary paralysis of a portion of the intestines that occurs typically after an abdominal surgery. The muscle of the bowel wall is transiently impaired and fails to transport intestinal contents. This lack of coordinated propulsive action leads to the accumulation of gas and fluids within the bowel. Patients with ileus are immobilized, have discomfort and pain, and are at increased risk for pulmonary complications.

Postoperative ileus occurs in approximately 50% of patients who undergo major abdominal surgery. Although ileus is most often seen following surgery, it may also be caused by sepsis, drugs (eg, opioids, antacids, warfarin, amitriptyline, chlorpromazine), metabolic problems (e.g., low potassium, magnesium, or sodium levels; anemia; hyposmolality), myocardial infarction, pneumonia, trauma (eg, fractured ribs, fractured spine), biliary colic and renal colic, head injury and neurosurgical procedures, intra-abdominal inflammation and peritonitis, and retroperitoneal hematomas.

Postoperative ileus is mediated via activation of inhibitory spinal reflex arcs. Intestinal inflammation triggered by handling of the intestine is thought to be the main mechanism. Local inflammation inhibits not only the contractile activity of the portion of the intestine that was handled during surgery, but it also activates inhibitory neural pathways and possibly triggers inflammation at distant untouched areas, leading to a generalized impairment of gastrointestinal motility [G E BOECKXSTAENS and W J de Jonge. Neuroimmune mechanisms in postoperative ileus. Gut 2009; 58:1300-1311]. Consequently, minimal invasive surgery is preferred to minimize trauma that would cause ileus. At least three distinct reflexes are involved: ultrashort reflexes confined to the bowel wall, short reflexes involving prevertebral ganglia, and long reflexes involving the spinal cord. The long reflexes are the most significant. Spinal anesthesia, abdominal sympathectomy, and nerve-cutting techniques have been demonstrated to either prevent or attenuate the development of ileus.

Natural recovery from post-operative ileus ordinarily occurs within 3-5 days, with function regained successively by the small bowel, the stomach, and the colon. Patients are given intravenous hydration, medications that may produce ileus are discontinued (e.g., opiates) and nonsteroidal anti-inflammatory drugs are administered, possibly with a cyclooxygenase-2 selective agent (celecoxib) to counteract possible platelet dysfunction. Oral feeding is discontinued until the ileus resolves clinically, but enteral nutrition is found to be essential for enhanced recovery after surgery, and patients may be encouraged to chew gum to promote gastrointestinal motility. Lidocaine may be administered during and after abdominal surgery, and thoracic epidurals containing bupivacaine alone or in combination with opioids and selective opioid antagonists methylnaltrexone (Relistor) or alvimopan (Entereg) may also be administered.

Considering the discomfort of the patient and the costs associated with hospitalization for post-operative ileus, therapies are being developed to reduce its likelihood or shorten its duration [Michael D. JOHNSON and R. Matthew Walsh. Current therapies to shorten postoperative ileus. Cleveland Clinic Journal of Medicine November 2009 vol. 76 (11) 641-648]. Many of these involve administration of anti-inflammatory agents, such as mast cell stabilizers, nonsteroidal anti-inflammatory drugs, and interleukin-10. Administration of carbon monoxide, pretreatment with blocking antibodies to intracellular adhesion molecule-1 and lymphocyte function-associated antigen-1, inactivating macrophages, and preventing mast cell activation are also under investigation.

Electrical stimulation of the vagus nerve has also been shown to ameliorate postoperative ileus by inhibiting local intestinal inflammation [Borovikova L V, Ivanova S, Zhang M, Yang H, Botchkina G I, Watkins L R, Wang H, Abumrad N, Eaton J W, Tracey K J. Vagus nerve stimulation attenuates the systemic inflammatory response to endotoxin. Nature 2000; 405: 458-462; VANDERZANDEN E P, Snoek S A, Heinsbroek S E, Stanisor O I, Verseijden C, Boeckxstaens G E, Peppelenbosch M P, Greaves D R, Gordon S, De Jonge W J. Vagus nerve activity augments intestinal macrophage phagocytosis via nicotinic acetylcholine receptor alpha4beta2. Gastroenterology 2009; 137: 1029-1039, 1039.e1-e4; THE FO, Boeckxstaens G E, Snoek S A, Cash J L, Bennink R, Larosa G J, van den Wijngaard R M, Greaves D R, de Jonge W J. Activation of the cholinergic anti-inflammatory pathway ameliorates postoperative ileus in mice. Gastroenterology 2007; 133: 1219-1228; Patent applications US20080183237 and US20090157138, entitled Methods And Apparatus For Treating Ileus Condition Using Electrical Signals to ERRICO]. However, vagal nerve stimulation as ordinarily practiced is an invasive procedure, so some investigators have instead attempted to induce a vagal response indirectly, by chewing gum or by providing nutrition that is rich in lipids.

Use of noninvasive magnetic stimulation of the vagus nerve has been attempted or suggested to influence gastrointestinal mobility, but its use to treat post-operative ileus has only been mentioned tangentially [A. Shafik. Functional magnetic stimulation of the vagus nerve enhances colonic transit time in healthy volunteers. Techniques in Coloproctology Volume 3 (1999, No. 3), 123-126; Patent applications US20060178703, entitled Treating inflammatory disorders by electrical vagus nerve stimulation, to HUSTON et al.; US20090143831 Treating inflammatory disorders by stimulation of the cholinergic anti-inflammation pathway to HUSTON et al.; US20100222629 Method and apparatus for magnetic induction therapy, to BURNETT et al]. As described above, the magnetic stimulation device disclosed herein is not intended to generate a magnetic field within bodily tissue, so it would produce its effect through a different mechanism than conventional magnetic stimulation.

Treatment of post-operative ileus using the disclosed toroidal magnetic stimulator is illustrated in FIGS. 6 and 7, which shows its positioning at one suitable anatomical location. The toroidal magnetic stimulation device of the present invention 30 is initially positioned there. It is understood that the device 30 is connected via wires or cables (not shown) to an impulse generator 310 as in FIG. 1. Conducting medium (e.g., conducting gel) is dispensed to the patient's skin as described above (e.g., 29 in FIG. 7). The position and angular orientation of the device are then adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz., typically 20 Hz. The stimulation may be performed for 1 to 200 minutes, typically for 30 minutes. Typically, the treatment is performed once as needed but may also be performed repeatedly, e.g., once a week for 12 weeks. However, parameters of the stimulation may be varied in order to obtain a beneficial response, as indicated, for example, by enhanced contractile activity of the gastrointestinal tract and/or when inflammation that is associated with a decrease of contractile activity of the gastrointestinal tract is slowed, stopped, or prevented.

Alzheimer (or Alzheimer's) disease (AD) is the most common cause of dementia, affecting more than 5 million individuals in the United States. AD clinical decline and pathological processes occur gradually. Dementia is the end stage of many years of accumulation of pathological changes, which begin to develop decades before the earliest clinical symptoms occur. A pre-symptomatic phase occurs first, in which individuals are cognitively normal but some have AD pathological changes. This is followed by a second prodromal phase of AD, commonly referred to as mild cognitive impairment (MCI). The final phase in the evolution of AD is dementia, defined as impairments that are severe enough to produce loss of function.

Until recently, a definitive diagnosis of AD could only be made at the autopsy or by brain biopsy of an individual, by identifying amyloid plaques and neurofibrillary tangles (NFTs) in the association regions of the individual's brain, particularly in the medial aspect of the temporal lobe. Additional evidence of AD from an individual's autopsy or biopsy would include the presence of the following: the granulovacuolar degeneration of Shimkowicz, the neuropil threads of Braak, and neuronal loss with synaptic degeneration.

Amyloid precursor protein (APP) is a membrane protein that is concentrated in the synapses of neurons. APP is the precursor molecule whose proteolysis generates β-amyloid (Aβ), a peptide whose amyloid fibrillar form is the primary component of amyloid plaques found in the brains of AD patients.

Tau proteins, which are abundant in the central nervous system, stabilize microtubules. When tau proteins are defective and no longer stabilize microtubules properly, they can produce dementias, including AD. Defective tau protein will aggregate and twist into neurofibrillary tangles (NFTs), so that the protein is no longer available the stabilization of microtubules. As a result, the neuronal cytoskeleton falls apart, contributing to neuronal malfunction and cell death.

AD begins when cells abnormally process the amyloid precursor protein (APP), which then leads to excess production or reduced clearance of β-amyloid (Aβ) in the cortex. Excess of one or more forms of Aβ leads to a cascade, characterized by abnormal tau protein aggregation, synaptic dysfunction, cell death, and brain shrinkage. The detailed molecular mechanism of tau protein aggregation is unknown, but it is thought that extracellular deposits of Aβ in the brains of AD patients promote tau polymerization.

Inflammation and the immune system play a significant role in AD pathogenesis. The inflammatory components in AD include microglia and astrocytes, the complement system, and various inflammatory mediators (including cytokines and chemokines). Microglia are the resident immune cell types of the central nervous system, and in AD, microglia may cause damage by secretion of neurotoxins. When microglia become activated during inflammation, they also secrete a variety of inflammatory mediators including cytokines (TNF and interleukins IL-1β and IL-6) and chemokines (macrophage inflammatory protein MIP-1a, monocyte chemoattractant protein MCP-1 and interferon inducible protein IP-10) that promote the inflammatory state.

Microglia accumulate in locations that contain Aβ and are associated with the local toxicity of Aβ plaques. Whether the accumulated microglia contribute to the removal or deposition of plaque is now thought to depend on the detailed microenvironment of the accumulated microglia. Microglial cell activation and migration toward β-amyloid plaques precede the appearance of abnormally shaped neurites and the formation of neurofibrillary tangles. It has been shown that following microglial migration to the plaques, microglial-derived proinflammatory cytokine TNF-alpha is induced, which in turn induces accumulation of the aggregation-prone tau molecules in neurites via reactive oxygen species. [GORLOVY, P., Larionov, S., Pham, T. T. H., Neumann, H. Accumulation of tau induced in neurites by microglial proinflammatory mediators. FASEB J. 23, 2502-2513 (2009)]. Elevated levels of TNF also induce an increased expression of interleukin-1, which in turn increases production of the precursors that may be necessary for formation of β-amyloid plaques and neurofibrillary tangles. Thus, the secretion of TNF-alpha by microglia contributes to a cycle wherein tau aggregates to form tangles, β-amyloid plaques are formed, microglia aggregate to those plaques, and more TNF-alpha is secreted by microglia cells.

In addition to its proinflammatory functions, TNF-alpha is a gliotransmitter that regulates synaptic function in neural networks. In particular, TNF-alpha has been shown to mediate the disruption in synaptic memory mechanisms. Etanercept, a biologic antagonist of TNF-alpha, when delivered by perispinal administration, has been shown to improve the cognitive abilities of AD patients, even within minutes of its administration [Edward L TOBINICK and Hyman Gross. Rapid cognitive improvement in Alzheimer disease following perispinal etanercept administration. Journal of Neuroinflammation 2008, 5:2; W Sue T GRIFFIN. Perispinal etanercept: Potential as an Alzheimer therapeutic. Journal of Neuroinflammation 2008, 5:3; Edward TOBINICK. Tumour Necrosis Factor Modulation for Treatment of Alzheimer's Disease Rationale and Current Evidence. CNS Drugs 2009; 23 (9): 713-725]. Furthermore, in a population of adults with rheumatoid arthritis, CHOU et al. observed that the risk of AD was significantly reduced by TNF inhibitor therapy for the rheumatoid arthritis, but not by other disease modifying agents used for treatment of rheumatoid arthritis. It may therefore be concluded that TNF may be an important component in the pathogenesis of AD [Richard C. CHOU, Michael A. Kane, Shiva Gautam and Sanjay Ghirmire. Tumor Necrosis Factor Inhibition Reduces the Incidence of Alzheimer's Disease in Rheumatoid Arthritis Patients. Program abstracts of the American College of Rheumatology/Association of Rheumatology Health Professionals Scientific Meeting, Nov. 8, 2010, Atlanta Ga., Presentation No. 640].

With the ability to better stage the progression of AD through use of biomarkers, treatment of AD may be justified at stages prior to actual dementia. With a better understanding of the pathogenesis of AD, those treatments might be directed to slowing, stopping, or reversing the pathophysiological processes underlying AD.

Biomarkers are cognitive, physiological, biochemical, and anatomical variables that can be measured in a patient that indicate the progression of AD. The most commonly measured biomarkers are decreased Aβ42 in the cerebrospinal fluid (CSF), increased CSF tau, decreased fluorodeoxyglucose uptake on PET (FDG-PET), PET amyloid imaging, and structural MRI measures of cerebral atrophy. Biomarkers of Aβ deposition become abnormal early, before neurodegeneration and clinical symptoms occur. Biomarkers of neuronal injury, dysfunction, and neurodegeneration become abnormal later in the disease. Cognitive symptoms are directly related to biomarkers of neurodegeneration, rather than to biomarkers of Aβ deposition.

At the present time, other than physical and mental exercise, only symptomatic therapies for AD are available. All approved drugs for the symptomatic treatment of AD modulate neurotransmitters—either acetylcholine or glutamate: cholinesterase inhibitors and partial N-methyl-D-aspartate antagonists. Psychotropic medications are also used to treat secondary symptoms of AD such as depression, agitation, and sleep disorders.

Therapies directed to modifying AD progression itself are considered investigational. These include treatment of the intense inflammation that occurs in the brains of patients with AD, estrogen therapy, use of free-radical scavengers, therapies designed to decrease toxic amyloid fragments in the brain (vaccination, anti-amyloid antibodies, selective amyloid-lowering agents, chelating agents to prevent amyloid polymerization, brain shunting to improve removal of amyloid, and beta-secretase inhibitors to prevent generation of the A-beta amyloid fragment), and agents that may prevent or reverse excess tau phosphorylation and thereby diminish formation of neurofibrillary tangles.

However, it is increasingly recognized that a single target or pathogenic pathway for the treatment of AD is unlikely to be identified. The best strategy is a multi-target therapy that includes multiple types of treatments [Mangialasche F, Solomon A, Winblad B, Mecocci P, Kivipelto M. Alzheimer disease: clinical trials and drug development. Lancet Neurol. 2010 July; 9(7):702-16]. Targets in that multi-target approach will include inflammatory pathways, and several therapeutic agents have been proposed to target them—nonsteroidal anti-inflammatory drugs, statins, RAGE antagonists and antioxidants [Stuchbury G, Munch G. Alzheimer associated inflammation, potential drug targets and future therapies. J Neural Transm. 2005 March; 112(3):429-53]. Another such agent, Etanercept, was mentioned above as targeting TNF-alpha, but its use has the disadvantage that because it does not pass the blood-brain barrier (BBB), its administration is via a painful spinal route or via an experimental method to get through the BBB [U.S. Pat. No. 7,640,062, entitled Methods and systems for management of alzheimer's disease, to SHALEV]. One TNF-inhibitor that does not have this disadvantage is thalidomide [Tweedie D, Sambamurti K, Greig N H: TNF-alpha Inhibition as a Treatment Strategy for Neurodegenerative Disorders: New Drug Candidates and Targets. Curr Alzheimer Res 2007, 4(4):375-8]. However, thalidomide is well known by the public to cause birth defects, and in a small trial, its use did not appear to improve cognition in AD patients [Peggy PECK. IADRD: Pilot Study of Thalidomide for Alzheimer's Disease Fails to Detect Cognitive Benefit but Finds Effect on TNF-alpha. Doctor's Guide Global Edition, Jul. 26, 2002]. There is therefore a need in the art for new therapies that target TNF-alpha, including its physiological activity for a given amount, as a component of a multi-target approach to treating AD.

In 2002, it was reported that electrical stimulation of the vagus nerve has a beneficial effect on cognition in patients with AD [Sjögren M J, Hellström P T, Jonsson M A, Runnerstam M, Silander H C, Ben-Menachem E. Cognition-enhancing effect of vagus nerve stimulation in patients with Alzheimer's disease: a pilot study. J Clin Psychiatry. 2002 November; 63(11):972-80]. The rationale for the trial was that vagus nerve stimulation had previously been found to enhance the cognitive abilities of patients that were undergoing vagus nerve stimulation for other conditions such as epilepsy and depression, as well cognitive abilities observed in animal studies. Results concerning the AD patients' improved cognitive abilities over a longer period of time, along with improvement in tau protein of cerebrospinal fluid, were subsequently reported [Merrill C A, Jonsson M A, Minthon L, Ejnell H, C-son Silander H, Blennow K, Karlsson M, Nordlund A, Rolstad S, Warkentin S, Ben-Menachem E, Sjögren M J. Vagus nerve stimulation in patients with Alzheimer's disease: Additional follow-up results of a pilot study through 1 year. J Clin Psychiatry. 2006 August; 67(8):1171-8]. Stimulation of the vagus nerve to treat dementia might be more effective than stimulation of nerves found in locations such as the spine, forehead, and earlobes [Cameron M H, Lonergan E, Lee H. Transcutaneous Electrical Nerve Stimulation (TENS) for dementia. Cochrane Database of Systematic Reviews 2003, Issue 3. Art. No.: CD004032. (2009 update)]. The method of using vagal nerve stimulation to treat AD had been disclosed earlier in U.S. Pat. No. 5,269,303, entitled Treatment of dementia by nerve stimulation, to Wernicke et al., but neither that patent nor the clinical trials proposed any physiological intermediary through which vagal nerve stimulation may result in clinical improvement to AD patients.

It has been proposed that electrical stimulation of the vagus nerve may attenuate an inflammatory response. In particular, methods involving electrical stimulation of the vagus nerve have been disclosed for attenuating or inhibiting the release of the pro-inflammatory cytokine TNF-alpha, including AD as one disease in a long list of diseases involving inflammation [U.S. Pat. No. 6,610,713, entitled Inhibition of inflammatory cytokine production by cholinergic agonists and vagus nerve stimulation, to TRACEY; Kevin J. Tracey. The inflammatory reflex. Nature 420: 853-859 (19 Dec. 2002); Kevin J. Tracey. Physiology and immunology of the cholinergic antiinflammatory pathway. J. Clin. Invest. 117:289-296 (2007)]. It has also been proposed that electrical stimulation of nerves of the sympathetic nervous system (particularly the splenic nerve) may also attenuate an inflammatory response, by attenuating or inhibiting the release of TNF-alpha, including AD as a one disease in a long list of diseases involving inflammation [U.S. Pat. No. 7,769,442, entitled Device and method for inhibiting release of pro-inflammatory mediator, to SHAFER]. PROLO et al. noted the above-mention vagal nerve stimulation investigations and predicted that interventions based on attenuation of inflammation would be useful for the treatment of AD [Paolo PROLO, Francesco Chiappelli, Alberto Angeli, Andrea Dovio, Maria Luisa Sartori, Fausto Fanto, Negoita Neagos, Ercolano Manfrini. Putative Neurolmmune Mechanisms in Alzheimer's Disease: Modulation by Cholinergic Anti-Inflammatory Reflex (CAIR). International Journal of Integrative Biology 2007, Vol 1 (No. 2):88-95].

However, as noted above, TNF-alpha is involved in more than inflammation in AD [Ian A. CLARK, Lisa M. Alleva and Bryce Vissel. The roles of TNF in brain dysfunction and disease. Pharmacology & Therapeutics, 128 (Issue 3, December 2010): 519-548]. It is also a gliotransmitter that regulates synaptic function in neural networks [Gertrudis PEREA and Alfonso Araque. GLIA modulates synaptic transmission. Brain Research Reviews. 63 (Issues 1-2, May 2010):93-102]. In that capacity, TNF-alpha has been shown to mediate the disruption in synaptic memory mechanisms. Furthermore, none of the above-mentioned citations have proposed that stimulation of the vagus nerve modulates the capacity of TNF-alpha to function as a gliotransmitter, which can be released from any glial cell, including oligodendrocytes, astrocytes, and microglia. Such modulation in capacity can be due to a change in the amount of TNF-alpha or in the activity of a given amount of TNF-alpha or in the activity of the cells between which TNF-related gliotransmission occurs. In fact, the above-mentioned citations are concerned only with the attenuation or inhibition of the release of TNF-alpha as a pro-inflammatory mediator, but not with its degradation or modification or with changes in its activity for a given amount.

Magnetic stimulation of AD patients has been performed, but its use has been intended to affect cognitive skills using transcranial magnetic stimulation [Mamede de Carvalho, Alexandre de Mendonga, Pedro C. Miranda, Carlos Garcia and Maria Lourdes Sales Luis. Magnetic stimulation in Alzheimer's disease. Journal of Neurology 244 (1997, No. 5): 304-307; Cotelli M, Manenti R, Cappa S F, Zanetti O, Miniussi C. Transcranial magnetic stimulation improves naming in Alzheimer disease patients at different stages of cognitive decline. Eur J Neurol. 2008 December; 15(12):1286-92; Guse B, Falkai P, Wobrock T. Cognitive effects of high-frequency repetitive transcranial magnetic stimulation: a systematic review. J Neural Transm. 2010 January; 117(1):105-22]. Furthermore, as described above, the device disclosed herein is not intended to generate a magnetic field within bodily tissue, so its use would not be a direct comparison with conventional magnetic stimulation.

Accordingly, a method is disclosed to treat AD patients, preferably as part of a multi-target therapy, which is to stimulate one or more nerves that modulate the capacity of TNF-alpha to function as a gliotransmitter (including modulating the activity of the cells between which TNF-related gliotransmission occurs) and/or that modulate the degradation of TNF-alpha, and/or modify the activity of existing TNF-alpha molecules as a pro-inflammatory mediator. In the preferred embodiment, the method stimulates the vagus nerve as indicated in FIGS. 6 and 7, using the toroidal magnetic stimulation device that is disclosed herein. The position and angular orientation of the device are adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz., typically 20 Hz. The stimulation may be performed for 1 to 200 minutes, typically for 30 minutes. Typically, the treatment is performed repeatedly, e.g., once a week for six months. However, parameters of the stimulation may be varied in order to obtain a beneficial response, as indicated, for example, by the measurement of TNF-alpha levels and/or activities in the patient's peripheral circulation and/or in the patient's cerebrospinal fluid, during and subsequent to each treatment.

Postoperative cognitive dysfunction (POCD) is a loss in cognitive function after surgery. The loss may include memory, the ability to learn, the ability to concentrate, and/or the ability to reason and comprehend. POCD does not refer to delirium that may occur immediately after surgery, but instead refers to loss that may persist weeks, months, or permanently after the surgery. The cognitive decline may be subtle, such that psychological testing is needed to detect it, or it may be profound and obvious.

A limited number of studies have been conducted to evaluate whether certain demographic populations are at higher risk to suffer from POCD, whether the risk is contingent on the type of surgery, whether the risk depends on the anesthesia that was used, how the medical condition of the patient prior to the surgery influences the risk, whether drug sensitivity is involved, and whether these variables influence the duration of the POCD, its preventability, or its treatability. Elderly patients are at greatest risk for developing POCD. A low level of education predisposes a risk of POCD. Patients undergoing cardiac surgery are at greatest risk, especially those with progressive atherosclerosis. However, major surgery in general poses a greater risk of developing POCD than minor surgery. The incidence of prolonged POCD is apparently similar regardless of the anesthetic technique used, suggesting that nonanesthetic factors are likely to be important. However, regional anesthesia decreases the incidence of POCD early after surgery. [Lars S. RASMUSSEN. Postoperative cognitive dysfunction: Incidence and prevention. Best Practice & Research Clinical Anaesthesiology 20(2006, No. 2): 315-330; Ola A. SELNES and Guy M. McKhann. Neurocognitive Complications after Coronary Artery Bypass Surgery. Ann Neurol 2005; 57:615-621; Ramesh RAMAIAH and Arthur M. Lam. Postoperative Cognitive Dysfunction in the Elderly. Anesthesiology Clin 27(2009): 485-496; Anne-Mette SAUER, Cornelis Kalkman and Diederik van Dijk. Postoperative cognitive decline. J Anesth (2009) 23:256-259].

The pathophysiology of POCD has been investigated in view of the above clinical findings and in the context of cellular responses to surgery in general [Niamh Ni CHOILEAIN and H. Paul Redmond. Cell response to surgery. Arch Surg 2006; 141:1132-40; XIE G L, Zhang W, Chang Y Z, Chu Q J. Relationship between perioperative inflammatory response and postoperative cognitive dysfunction in the elderly. Med Hypotheses 2009; 73:402-3; HU Z, Ou Y, Duan K, Jiang X. Inflammation: a bridge between postoperative cognitive dysfunction and Alzheimer's disease. Med Hypotheses. 2010 April; 74(4):722-4].

Although the cause of POCD appears to be multifactorial, the response of the body to the surgery itself appears to be a primary contributing factor. This is because decreased surgical trauma is associated with a decreased risk of POCD, and the stress of surgery triggers an inflammatory response with release of cytokines that may be responsible for changes in brain function and recovery. Furthermore, a correlation has been observed in patients' interleukin-6, cortisol and late functional recovery. Animal experiments also indicate that there is a relation between cytokine-mediated inflammation and POCD [Y WAN, J Xu, D Ma, Y Zeng, M Cibelli, M Maze. Postoperative impairment of cognitive function in rats: a possible role for cytokine-mediated inflammation in the hippocampus. Anesthesiology 2007; 106:436-43].

There is currently no generally agreed-upon treatment for POCD. Primary prevention by providing good oxygenation and cerebral perfusion during surgery, and adequate analgesia and emotional support after surgery have been suggested, including the use of occupational therapy and biofeedback. Medical conditions that could also contribute to POCD should also be treated, such as hypothyroidism. Otherwise, there are few treatment options. XIONG et al suggested that transcutaneous stimulation of the vagus nerve may attenuate the inflammatory response that appears to be associated with POCD. Their suggestion was that the stimulation be transcutaneous because implantation of a vagal nerve stimulator by surgery may exacerbate the very surgery-induced problem that the stimulation is intended to treat. [XIONG J, Xue F S, Liu J H, Xu Y C, Liao X, Zhang Y M, Wang W L, Li S. Transcutaneous vagus nerve stimulation may attenuate postoperative cognitive dysfunction in elderly patients. Medical Hypotheses 73 (2009) 938-941].

However, the site of transcutaneous vagal stimulation that XIONG et al suggest is the external auditory canal. This may not be as effective as stimulating at the site where vagus nerve stimulators are ordinarily implanted, namely in the neck. Furthermore, XIONG et al do not suggest stimulation parameters that should be used. Accordingly, a method is disclosed here to better treat POCD patients. In the preferred embodiment, the method stimulates the vagus nerve in the neck as indicated in FIGS. 6 and 7, using the toroidal magnetic stimulation device that is disclosed herein. The position and angular orientation of the device are adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz., typically 20 Hz. The stimulation may be performed for 1 to 200 minutes, typically for 30 minutes. Typically, the treatment is performed repeatedly, e.g., once a week for six months. However, parameters of the stimulation may be varied in order to obtain a beneficial response, as indicated, for example, by the measurement of cytokines in the patient's peripheral circulation and/or in the patient's cerebrospinal fluid, or by psychological evaluation of the extent of the patient's cognitive dysfunction.

Rheumatoid arthritis (RA) is a chronic inflammatory disorder that primarily attacks the synovial membrane that lines joints and tendon sheaths. Joints in the hands, feet and spine are most often affected, but larger joints such as those in the shoulder and knee can also be affected. RA may also affect the skin, lungs, kidneys, blood cells and vessels, nervous system, liver, eyes, and bone. If not treated, it can be a very painful condition, resulting in a loss of functioning and mobility. 2.5 million Americans suffer from RA, with women being three times more likely to experience RA than men. Its onset is often between the ages of 40 to 50, but it can occur at any age. As RA progresses, inflammation causes tendon tethering and destruction of the joint surface, which limits movement and leads to deformity of the joints.

Although the cause of RA is unknown, autoimmunity plays a primary role in its onset and progression. Joint stiffness early in the morning is a prominent feature of RA, which typically lasts for more than an hour and may be relieved by movement. In contrast, pain due to other forms of arthritis, such as osteoarthritis, is less prominent in the morning, and movement may increase the pain. When RA is suspected clinically, immunological tests are performed for the presence of rheumatoid factor and anti-citrullinated protein antibodies. Other tests may be performed to rule out other causes or mimics of arthritis, such as lupus erythematosus, hemochromatosis, gout, Lyme disease, Reiter's disease, ankylosing spondylitis, Hepatitis C, sarcoidosis, amyloidosis, Whipple's disease, rheumatic fever or other bacterial causes of arthritis, or Still's disease.

In addition to the presence of rheumatoid factors and antibodies to citrullinated peptides, evidence for the presence and progression of RA includes a patient history of cigarette smoking, a genetic link with HLA-DR4 and related allotypes of MHC Class II and the T cell-associated protein PTPN22, a random pattern of bodily sites where and when individuals are affected by arthritis (as distinguished from arthritis occurring at sites where and when joints have worn from chronic use), disease progression that is significantly inhibited by blockade of the cytokine TNF-alpha, and disease progression that is inhibited by depletion of B lymphocytes without inhibition by depletion of T lymphocytes. The latter evidence suggests that abnormal B cell—T cell interaction plays a significant role in the pathophysiology of RA, wherein inflammation is driven either by B cell or T cell products stimulating release of TNF-alpha and other cytokines [Marc Feldmann FELDMANN and Ravinder N. MAINI. Role of cytokines in rheumatoid arthritis: an education in pathophysiology and therapeutics. Immunological Reviews 223 (Issue 1, June 2008):7-19; Iain B. McINNES and Georg Schett. Cytokines in the pathogenesis of rheumatoid arthritis. Nature Reviews Immunology 7(June 2007):429-442].

Treatment of RA includes the use of non-pharmacological therapy (physical therapy including rest and exercise, orthoses, occupational therapy and nutritional therapy), the use of analgesia and anti-inflammatory drugs to suppress the symptoms, and disease-modifying antirheumatic drugs (DMARDs) that are used to inhibit the underlying immune process. The DMARDs are most relevant here, because the treatment method that is disclosed below is also intended to inhibit the underlying immune process. The DMARDs are often used in combination and include methotrexate, hydroxychloroquine, sulfasalazine, minocycline, leflunomide, cyclosporine, and azathioprine. The DMARDs also include biologic drugs such as TNF-alpha blockers (etanercept, infliximab, adalimumab, certolizumab pegol, and golimumab), Interleukin 1 blockers (anakinra), monoclonal antibodies against B cells (rituximab), T cell costimulator blockers (abatacept), and Interleukin 6 blockers (tocilizumab).

DMARDs often have significant side effects, including nausea, vomiting, or diarrhea. They also cause liver problems and raise the risk of infection. They may cause white blood cell counts to decrease, and cause loss of red blood cells that may result in anemia. Accordingly, there is a need for effective disease-modifying treatments for RA that do not produce such side effects.

As described above in connection with the treatment of dysfunction associated with TNF-alpha in Alzheimer disease, electrical stimulation of the vagus nerve may produce a similar anti-inflammatory effect, for example, as a TNF-alpha blocker. In fact, VAN MAANEN et al suggest that the inflammation associated with RA might be treated by electrical stimulation of the vagus nerve. [Marjolein A. VAN MAANEN, Margriet J. Vervoordeldonk and Paul P. Tak. The cholinergic anti-inflammatory pathway: towards innovative treatment of rheumatoid arthritis. Nature Reviews Rheumatology 5(April 2009): 229-232]. They comment as follows: "A novel anti-inflammatory strategy could be developed by means of optimal VNS (vagal nerve stimulation) generated by a special device. No studies of VNS in RA have been published so far, but one case—control study has shown that the risk of developing RA is not increased after vagotomy". Such stimulation had been suggested earlier, for example, in patent application No. US20060178703, entitled Treating inflammatory disorders by electrical vagus nerve stimulation, to HUSTON et al, which lists rheumatoid arthritis in a long list of diseases that may be treated by electrical stimulation of the vagus nerve. However, they describe the method in terms of stimulation using electrodes, not stimulation with a magnetic stimulator.

An impediment to the treatment of RA by vagal nerve stimulation is that the stimulators are ordinarily implanted surgically. Consequently, patients may be reluctant to undergo surgery in order to treat inflammation that can be treated pharmacologically. Therefore, a method is disclosed here to treat RA non-invasively. In the preferred embodiment, the method stimulates the vagus nerve in the neck as indicated in FIGS. 6 and 7, using the toroidal magnetic stimulation device that is disclosed herein. The position and angular orientation of the device are adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz., typically 20 Hz. The stimulation may be performed for 1 to 200 minutes, typically for 30 minutes. Typically, the treatment is performed repeatedly, e.g., once a week for six months. However, parameters of the stimulation may be varied in order to obtain a beneficial response, as indicated, for example, by the measurement of cytokines in the patient's peripheral circulation, by mechanical tests that evaluate the patient's mobility, or by radiological examination of the patient's joints.

Another example of diseases that may be treated with the disclosed magnetic stimulator device is those diseases involving excessive constriction of bronchi in the lungs. They include asthma, anaphylactic shock, and chronic obstructive pulmonary disease. Asthma affects an estimated eight to thirteen million adults and children in the United States. Anaphylaxis ranks among the airway occluding disorders as the most deadly, claiming many deaths in the United States every year. Chronic obstructive pulmonary disease (COPD) is a major cause of disability, and is the fourth leading cause of death in the United States.

Applicant has made the unexpected discovery that stimulating a region of a patient's neck near the vagus nerve within a particular frequency range results in almost immediate and significant improvement in bronchodilation to counteract the bronchoconstriction. Applicant has further discovered that applying electrical impulses outside of the selected frequency range (15 Hz to 50 Hz) does not result in significant improvement. By way of example, at least one induced electrical signal may be of a frequency between about 15 Hz to 35 Hz. By way of example, at least one induced electrical signal may have a pulsed on-time of between about 50 to 1000 microseconds, such as between about 100 to 300 microseconds, or about 200 microseconds.

Details of such treatment of bronchoconstriction associated with asthma, anaphylaxis, and COPD, including treatment using a toroidal magnetic stimulation device, are disclosed in applicant's co-pending U.S. patent application Ser. No. 12/859,568 filed Aug. 19, 2010 entitled Non-invasive treatment of bronchial constriction, to SIMON, which is hereby incorporated by reference in its entirety.

The storage and voiding of urine are performed by the urinary bladder and urethra, which are muscular structures controlled by the sacral nerve. The urinary tract has two phases of activity: the storage phase, when urine is stored in the bladder, and the voiding phase, when urine is released through the urethra. During the storage phase, the muscular sphincter of the urethra contracts (blocking flow of urine), and the detrusor muscle of the bladder is relaxed. During the voiding phase, the reverse happens—the sphincter of the urethra relaxes (permitting flow of urine), and the detrussor muscle of the bladder contracts to force urine into the urethra. Nerve signals from stretch receptors in the bladder wall are sent to the pontine micturition center in the brainstem and to the cerebrum where voluntary actions are initiated. When the bladder fills and the bladder's stretch receptors are actively signaling that filled state, the conscious urge to urinate becomes difficult to ignore. Once the voluntary nerve signal to begin urination has been issued, that signal causes the smooth muscle of the bladder to contract and the urethral sphincter muscle to relax. The flow of urine through the urethra is then sensed by its receptors, and they send nerve signals which help sustain urination until the bladder is empty.

Individuals with an overactive bladder exhibit a sudden urge to urinate and a high frequency of urination, especially at night (nocturia). They often, but not always, also exhibit urge incontinence, which is leakage of urine due to bladder muscles that contract or spasm inappropriately. Often these contractions occur regardless of the amount of urine that is in the bladder. Urge incontinence may result from bladder outlet obstruction from an enlarged prostate, inflammation or infection, or neurological disorders. However, in most cases of urge incontinence, no specific cause can be identified.

Management options for overactive bladder include lifestyle adjustments, bladder retraining, pelvic floor exercises, biofeedback, and pharmacotherapy (e.g., anticholinergic antimuscarinic medications, such as oxybutynin, tolterodine, trospium chloride, derifenacin, solifenacin, and fesoterodine fumarate; as well as botox and capsaicin). Side effects and urinary retention occur in approximately 20% of those who use these medications. Major surgical procedures (e.g., bladder augmentation, Burch colposuspension and the pubovaginal sling) are considered last resorts, as they potentially lead to serious side effects.

If pharmacotherapy is unsuccessful and surgery is not being considered, patients with an overactive bladder are often treated by spinal nerve neuromodulation. Humans have 31 left-right pairs of spinal nerves, each roughly corresponding to a segment of the vertebral column: 8 cervical spinal nerve pairs (C1-C8), 12 thoracic pairs (T1-T12), 5 lumbar pairs (L1-L5), 5 sacral pairs (S1-S5) and 1 coccygeal pair. Sacral nerve modulation was developed based on the observation that the S2-S4 nerve roots provide the primary innervation to the bladder and urethra.

With sacral nerve modulation, patients first undergo a screening with percutaneous nerve evaluation, in which a temporary wire electrode is inserted in the S3 foramen. Patients who show a 50% or greater improvement in one or more urine voiding parameters after 3-7 days of electrode stimulation are offered a permanent implant. The permanent electrode is then implanted as follows. A midline sacral incision is made, the paravertebral muscles are separated, and an insulated electrode is placed in the S3 sacral foramen. Another incision is made over the upper buttock, creating a pocket in which the neurostimulator is placed. The electrode and stimulator are connected with leads, the incisions are closed, and after a week, the stimulator is programmed for therapeutic use. The procedure is expensive, and problems arise in up to a third of the patients, including change in bowel function, infection, lead movement, pain at implant sites, and/or unpleasant stimulation or sensation. The mechanism for sacral neuromodulation is unknown, but is probably multifactorial and impacts the neuroaxis at several different levels.

Percutaneous tibial nerve stimulation (PTNS) offers a safer, less invasive treatment alternative for overactive bladder than sacral nerve neuromodulation. Rather than requiring an incision and placement of electrodes in the sacrum, PTNS utilizes the nerve root S3 but at a location much closer to the surface of the skin, at the tibial nerve slightly above the ankle. The rationale is that the tibial nerve, a branch of the sciatic nerve, is derived from spinal nerves L4 through S3. Direct electrical stimulation of the tibial nerve was first reported by McGuire and colleagues in 1983, but its use for treating bladder and incontinence problems was developed by Stoller beginning in 1987 [Govier F E, Litwiller S, Nitti V, Kreder K J Jr, Rosenblatt P. Percutaneous afferent neuromodulation for the refractory overactive bladder: results of a multicenter study. J Urol. 2001 April; 165(4):1193-8].

To perform PTNS, a sensitive pressure point is identified approximately 3 finger breadths cephalad from the medial malleolus and about 1 finger breadth posterior from the edge of the tibia. A needle is inserted through the skin approximately 3 to 4 cm posterior to the tibia. The angle of the needle is 60 degrees cephalad from a perpendicular line along the length of the tibia. A ground pad is placed over the medial aspect of the calcaneus. A stimulator is then connected to the needle and the ground pad. A current 0.5-9 mA at 20 Hz provides stimulation. Each treatment session lasts 30 minutes, and the sessions are conducted weekly. After 12 months, statistically significant improvements compared with baseline are seen for frequency (2.8 fewer voids daily), urge incontinence (1.6 fewer episodes daily), nocturia (0.8 fewer void per night), and voided volume (39 more mL per void) and on subjective questionnaires. [Govier F E, Litwiller S, Nitti V, Kreder K J Jr, Rosenblatt P. Percutaneous afferent neuromodulation for the refractory overactive bladder: results of a multicenter study. J Urol. 2001 April; 165(4): 1193-8; MacDiarmid S A, Peters K M, Shobeiri A, et al. Long-term Durability of Percutaneous Tibial Nerve Stimulation for the Treatment of Overactive Bladder. J Urol. 2010; 183:234-240; van Balken M R, Vergunst H, Bemelmans B L. The use of electrical devices for the treatment of bladder dysfunction: a review of methods. J Urol. 2004 September; 172(3):846-51; Finazzi-Agro E, Petta F, Sciobica F, Pasqualetti P, Musco S, Bove P. Percutaneous tibial nerve stimulation effects on detrusor overactivity incontinence are not due to a placebo effect: a randomized, double-blind, placebo controlled trial. J Urol. 2010 November; 184(5):2001-6].

Conventional magnetic stimulation has been used previously to treat urinary incontinence and overactive bladder, but those investigations did not involve stimulation of the tibial nerve near the ankle as in PTNS [Galloway N T, El-Galley R E, Sand P K, Appell R A, Russell H W, Carlin S J. Extracorporeal magnetic innervation therapy for stress urinary incontinence. Urology 1999; 53: 1108-11; Fujishiro T, Takahashi S, Enomoto H, Ugawa Y, Ueno S, Kitamura T. Magnetic stimulation of the sacral roots for the treatment of urinary frequency and urge incontinence: an investigational study and placebo controlled trial. J Urol. 2002 September; 168(3):

1036-9; Takahashi S and Kitamura T. Overactive bladder: magnetic versus electrical stimulation. Current Opinion in Obstetrics & Gynecology 2003, 15(5):429-33; But I. Conservative treatment of female urinary incontinence with functional magnetic stimulation. Urology. 2003 March; 61(3): 558-61.; Gilling P J, Wilson L C, Westenberg A M, McAllister W J, Kennett K M, Frampton C M, et al. A double-blind randomized controlled trial of electromagnetic stimulation of the pelvic floor vs sham therapy in the treatment of women with stress urinary incontinence. BJU International 103 (Issue 10, May 2009): 1386-1390; Nobuyuki KAI, Masakazu KAWAJIRI, Narihito SEKI, Naruaki TAKANO, Jun-ichi KIRA, Shozo TOBIMATSU, and Seiji NAITO. Efficacy of High-frequency Magnetic Stimulation of the Sacral Root in Patients with Urinary Incontinence Following a Radical Prostatectomy. LUTS (2010) DOI: 10.1111/j.1757-5672.2010.00062.x, pp. 1-5].

The method and devices disclosed in the following patents deal with incontinence but are not adapted to the PTNS method described above: U.S. Pat. No. 5,984,854 Method for treating urinary incontinence and an apparatus therefor, to Ishikawa; and U.S. Pat. No. 6,086,525 Magnetic nerve stimulator for exciting peripheral nerves to Davey et al. A family of applications related to patent application US20100222629 Method and apparatus for magnetic induction therapy, to BURNETT et al uses an unconventional adjustable coil that neither passes high current through the coil nor uses a core to increase the stimulus. It appears not to be designed to stimulate the tibial nerve as deeply or as powerfully as the device disclosed herein. Furthermore, as described above, the device disclosed herein is not intended to generate a magnetic field within bodily tissue.

A therapeutic application of the disclosed toroidal magnetic stimulation device is to treat urinary incontinence and/or overactive bladder by stimulating the tibial nerve at or near a location at which PTNS is performed. It is non-invasive and eliminates any pain associated with repeated needle-puncture. In fact, it produces minimal pain, if any. Furthermore, training to perform the procedure with the disclosed toroidal magnetic stimulator is minimal, in contrast to PTNS, which requires significant training in order to insert a needle in a safe manner.

Figure 8:
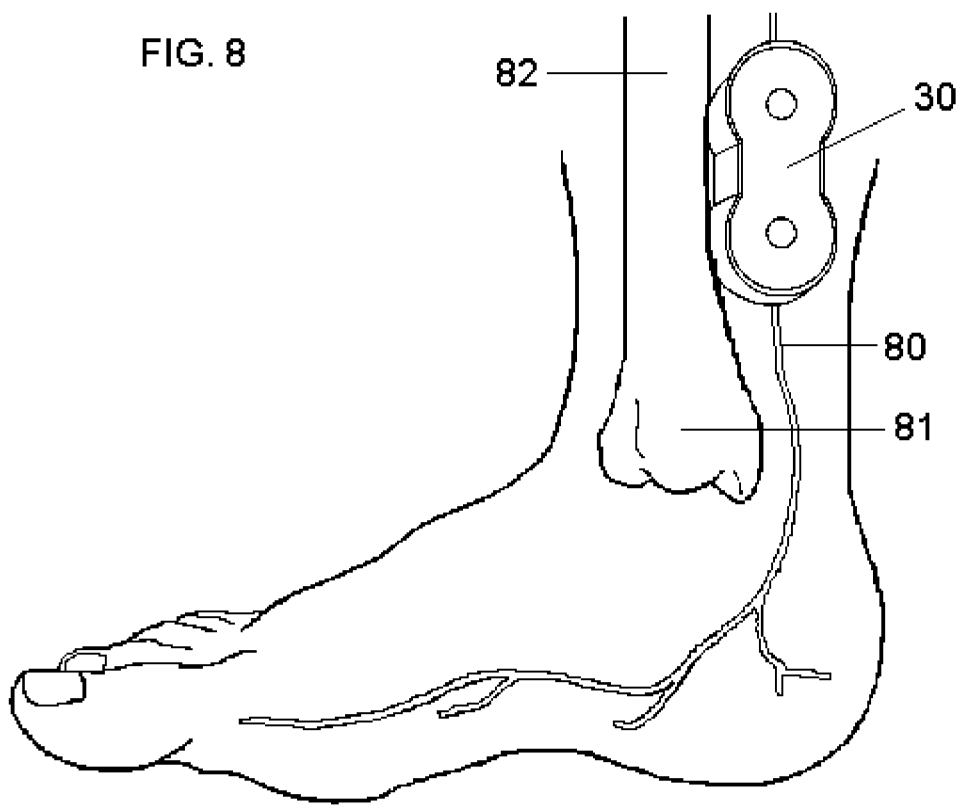
FIG. 8 illustrates a method to treat urinary incontinence and/or overactive bladder, wherein a stimulator coil according to the present invention is positioned at a location above the ankle in order to stimulate the tibial nerve.

Treatment with the disclosed stimulator at a suitable location is illustrated in FIG. 8. The method stimulates the tibial nerve 80, which runs down the leg and into the foot as indicated. To perform the stimulation, the toroidal magnetic stimulation device of the present invention 30 is positioned approximately 3 finger breadths cephalad from the protruding medial malleolus 81 and about 1 finger breadth posterior from the edge of the tibia 82. It is understood that the device 30 is connected via wires or cables (not shown) to an impulse generator 310 as in FIG. 1. Conducting medium (e.g., conducting gel) is dispensed to the patient's skin as described above (e.g., 29 in FIG. 7). The position and angular orientation of the device are then adjusted about that location until the patient perceives stimulation when current is passed through the coils. The applied current is increased gradually, first to a level wherein the patient feels sensation anywhere there is innervation of the tibial nerve, as indicated for example by flexing of the big toe and/or fanning or plantar toe flexion of ipsilateral digits 2 through 5. The power is then increased, but is set to a level that is less than one at which the patient first indicates any discomfort. Straps, harnesses, or frames are used to maintain the stimulator in position (not shown in FIG. 8). The stimulation is then performed typically with a fixed pulse width of 200 microseconds at a frequency of 20 Hz for 30 minutes. Typically, the treatment is performed once a week for 12 weeks. Treatment may be performed near either or both ankles. However, parameters of the stimulation may be varied in order to obtain a beneficial response, as indicated for example, by the patient experiencing on average fewer daily urinary voids, and/or fewer daily episodes of urge incontinence, and/or fewer urinary voids per night, and/or increased urinary volumes per void, and/or improved patient emotional well-being.

The sphincter of Oddi (SO), located at the junction of the bile and pancreatic ducts with the duodenum (small intestine), comprises a ring of smooth muscle that is controlled by the autonomic nervous system and other factors. The primary functions of the SO are to relax to allow the delivery of bile (produced in the liver; stored in the gallbladder) and pancreatic juice into the duodenum, and to contract (constrict) to prevent the reflux of duodenal contents into the biliary and pancreatic systems.

The SO exhibits a basal level of muscular contraction, upon which is superimposed spontaneous phasic contractions and relaxations that resemble peristalsis. Contraction and relaxation of the SO is controlled by the autonomic nervous system via the anterior and posterior hepatic plexuses, consisting of postganglionic fibers from the coeliac ganglion, and preganglionic para-sympathetic fibers from the left and right vagus nerves. Neuronal reflexes connecting the SO with the stomach, duodenum, and gallbladder coordinate the activity of these organs. Bioactive chemicals (e.g. from food) and inflammation also modulate contraction of the SO.

Disordered motility of the SO is associated with the most common functional disorders of the biliary tract and pancreas. In these disorders, the SO exhibits muscular spasms or is abnormally constricted, often due to hypertensive smooth muscle contraction. As a consequence, pressures within the bile and pancreatic ducts also become abnormal, and the flow of material within the ducts may become obstructed.

Patients who present with biliary SO dysfunction typically experience severe, recurrent biliary type pain, often 4-5 years after removal of the gallbladder (cholecystectomy), and are mostly female. Pancreatic SO dysfunction presents as recurrent episodes of pancreatitis without an obvious cause.

Other than symptomatic treatment, there is no established medical therapy for patients suffering SO dysfunction. To date, the most effective form of therapy for SO dysfunction is endoscopic sphincterotomy. However, in a significant number of sphincterotomy cases, the patient's pain recurs or other complications arise [Cotton P B, Lehman G, Vennes J, Geenen J E, Russell R C, Meyers W C, et al. Endoscopic sphincterotomy complications and their management. Gastrointest Endosc 1991; 37:383-93].

GUELRUD et al. demonstrated that transcutaneous electrical nerve stimulation (TENS) used in patients with sphincter of Oddi dysfunction decreased basal sphincter pressure, although not to normal values [Guelrud M, Rossiter A, Souney P F, Mendoza S, Mujica V. The effect of transcutaneous nerve stimulation on sphincter of Oddi pressure in patients with biliar dyskinesia. Am J Gastroenterol 1991; 86:581-585]. The negative electrode was placed on the dorsal web between the first and second metacarpal bones, and a positive electrode was placed at the ulnar border of the same hand. Pulses of 0.1 ms duration at 6 Hz and 10-20 mA current were delivered until rhythmic flexion of the fingers could be performed without producing pain. Stimulation was performed for 45 minutes.

BLAUT et al. extended that investigation by showing that TENS also decreases intraductal biliary pressure, which may underly the pain associated with SO dysfunction [Urszula BLAUT, Jerzy Marecik, Artur Hartwich, Roman M. Herman, Janusz Laskiewicz and Piotr J. Thor. The effect of transcutaneous nerve stimulation on intraductal biliary pressure in post cholecystectomy patients with T-drainage. Eur J Gastroenterol Hepatol (2003) 15:21-26]. The negative electrode was placed on the ulnar edge of the forearm in the proximal one-third of its length, and the positive electrode was placed on the abdomen in the point indicated by crossing the rectus abdominis muscle and costal margin. Stimulation was performed with the following parameters: 2 bursts/s, 7 pulses/burst, 100 Hz intraburst rate, 230 microsecond pulse width. The wave form of an isolated pulse was balanced rectangularly (zero net DC component) and the pulse amplitude was 10-30 mA, depending on the subject's sensitivity. The amplitude was increased until the patient reported a light 'tingling' at the sites of electrode placement. Each session lasted 15 min.

These investigators did not identify any particular nerve as being the target of stimulation. In another investigation, LEE et al used electroacupuncture to stimulate acupoint GB34 to achieve relaxation of the SO that reversed immediately upon cessation of stimulation. [Sung-Koo Lee, Myung-Hwan Kim, Hong-Ja Kim, Dong-Wan Seo, Kyo-Sang Yoo, Yun-Ho Joo, Young-II Min, Ji-Hoon Kim, Byung-Il Min. Electroacupuncture may relax the sphincter of Oddi in humans. Gastrointestinal Endoscopy 53, (No. 2, 2001): 211-216.] That acupuncture point is located below the lateral aspect of the knee, in the tender depression approximately 1 cm anterior and inferior to the head of the fibula. However, because they stimulated only an acupoint, they too did not identify any particular nerve as being the target of stimulation.

In investigations involving anesthatized rabbits and cats, CHIU et al. stimulated spinal nerves in the 6th and 7th intercostal space in the right midclavicular line. The effect was to only indirectly increase SO contractile activity in rabbits but decrease the SO activity in cats, through increased secretion of cholecystokinin [Chiu J H, Kuo Y L, Lui W Y, Wu C W, Hong C Y. Somatic electrical nerve stimulation regulates the motility of sphincter of Oddi in rabbits and cats: evidence for a somatovisceral reflex mediated by cholecystokinin. Dig Dis Sci. 1999 September; 44(9):1759-67].

In patent application US20080195171, entitled Method and Apparatus for Electrical Stimulation of the Pancreatico-Biliary System, to SHARMA, stimulation of sympathetic autonomic nerves innervating the pancreaticobiliary system is disclosed as an indirect way of preventing or treating sphihcter of Oddi dysfunction, through the lowering of pancreaticobiliary ductal pressures. Patent application US20090192557, entitled Methods and systems of treating pancreatitis pain caused by sphincter of Oddi dysfunction, to WHITEHURST et al discloses methods of treatment using an implanted stimulator. In U.S. Pat. No. 7,720,540, entitled Pancreatitis treatment KNUDSON et al, methods are disclosed to treat pancreatitis, but mention is not made of treating the sphincter of Oddi specifically.

Patent application US20070106338, entitled Direct and Indirect Control of Muscle for the Treatment of Pathologies to ERRICO discloses treatments that more generally apply a the signal to the nerves that innervate or modulate function of the Sphincter of Oddi. In patent application US20100249873, entitled Direct and Indirect Control of Muscle for the Treatment of Pathologies, to ERRICO, the sphincter of Oddi may be stimulated by direct application of electrical stimulation to the smooth muscles of the sphincter, or by modulation of the signals applied to the sphincter through the hepatic plexus. That disclosure contemplates applying an electrical stimulation signal to at least one nerve fiber, such that relaxation of at least one smooth muscle of a patient's sphincter of Oddi is affected and reduced bile pressure in the patient's biliary duct is affected. This may be achieved by applying the stimulatory signal to nerves emanating from a patient's sympathetic nerve chain. Alternatively, this may be achieved by applying the stimulation to nerve fibers emanating from the patient's tenth cranial nerve. That disclosure indicates that it is preferable that the stimulation be applied to the nerve plexus of fibers emanating from both the sympathetic nerve chain and the tenth cranial nerve (the vagus nerve), and this is most preferably the hepatic plexus.

A family of applications related to patent application US20100222629, entitled Method and apparatus for magnetic induction therapy, to BURNETT et al mentions treatment of sphincter of Oddi disorder among a long list of diseases. That application discloses an unconventional adjustable coil that neither passes high current through the coil nor uses a core to increase the stimulus. It is therefore not designed to stimulate nerves or tissue as deeply or as powerfully as the device disclosed herein. Furthermore, as described above, the device disclosed herein is not intended to generate a magnetic field within bodily tissue, so use of the present invention would function differently than the one disclosed by BURNETT et al.

A therapeutic application of the disclosed toroidal magnetic stimulation device is to treat Sphincter of Oddi dysfunction. This comprises stimulation with the device at or near any of the nerve or tissue structures that were described in the publications or patent applications that were cited above.

Figure 9:
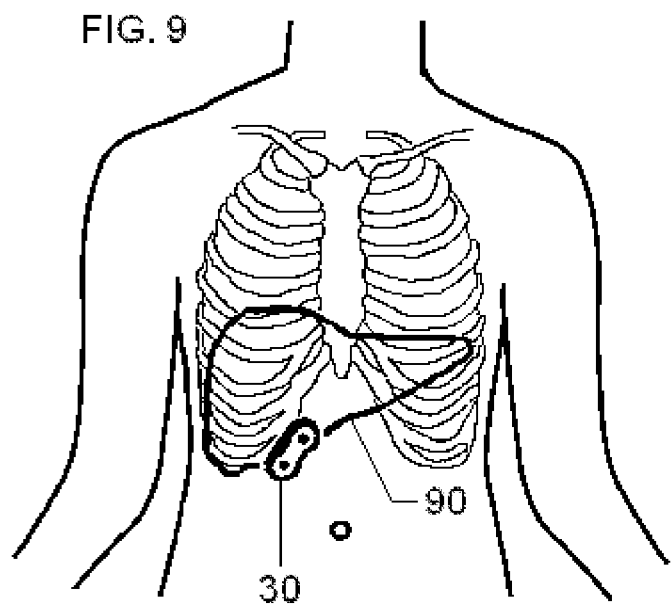
FIG. 9 illustrates a method to treat Sphincter of Oddi dysfunction, wherein the stimulator coil according to the present invention stimulates a patient at a location above the liver and adjacent to the rib cage.

Treatment of Sphincter of Oddi dysfunction using the disclosed toroidal magnetic stimulator is illustrated in FIG. 9, which shows its positioning at one suitable anatomical location. Other locations are also possible, and more than one stimulation device may be used simultaneously, for example, at the location indicated in FIG. 9 and also at the vagus nerve location indcated in FIG. 6. Referring to FIG. 9, the toroidal magnetic stimulation device of the present invention 30 is initially positioned under the ribs and over the liver 90 as indicated. It is understood that the device 30 is connected via wires or cables (not shown) to an impulse generator 310 as in FIG. 1. Conducting medium (e.g., conducting gel) is dispensed to the patient's skin as described above (e.g., 29 in FIG. 7). The position and angular orientation of the device are then adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 9). The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz, typically 20 Hz. The stimulation may be performed for 1 to 200 minutes, typically for 30 minutes. Typically, the treatment is performed once as needed but may also be performed repeatedly, e.g., once a week for 12 weeks. However, parameters of the stimulation may be varied in order to obtain a beneficial response, as indicated, for example, by testimony from the patient concerning the experience of pain attributable to Sphincter of Oddi dysfunction, during and subsequent to each treatment. The stimulation parameters may also be adjusted to cause the patient to experience decreased basal sphincter of Oddi pressure, and/or decreased sphincter of Oddi muscular spasms, and/or decreased pressures within the bile and/or pancreatic ducts, and/or increased flow of material within the bile and/or pancreatic ducts, and/or decreased biliary-type pain, and/or decreased episodes of pancreatitis.

For applications in which it is necessary to position the stimulator accurately, for example, to stimulate precisely the same anatomical location on multiple occasions, a method may be employed to position the stimulator to the desired location. This may be accomplished using a method now disclosed, which is illustrated by the example shown in FIG. 10. The example relates to stimulation of the brain (transcranial stimulation), but the method may be adapted to other anatomical locations by using holders that are configured to correspond to the anatomical geometry of the other locations.

The disclosed method is motivated by the observation that the low-current stimulator disclosed herein is compact, lightweight, and may be used over an extended period of time without concern for over-heating or for significant discomfort to the patient (unlike high current magnetic stimulators). The principle underlying the positioning method is that the stimulator produces eddy currents, i.e., induced currents that flow in closed paths in the absence of an anode and cathode. The method also relies on the observation that the magnitude of those currents is a function of the conductance of the biological material that is being stimulated.

Electrical impedance is the total opposition that a circuit (in this case, the stimulator coil(s), including the conducting material with which it is in contact) presents to alternating current. Impedance is measured in ohms and may include resistance, inductive reactance, and capacitive reactance. Vectors are used to specify total impedance, separating the resistance and reactance components. Because the biological material that is being stimulated contributes to the electrical impedance of the coil that is being used to induce the eddy currents, variations in electrical conductivity of the tissue being stimulated will result in corresponding variations of impedance, when the impedance of the stimulating coil is measured as it is applied to the body. Such impedance measurements may be made by devices that are commercially available, e.g., Agilent 4294A Precision Impedance Analyzer [Agilent Impedance Measurement Handbook. A guide to measurement technology and techniques 4th Edition, Agilent Technologies, Inc., 5301 Stevens Creek Blvd Santa Clara Calif. 95051].

By scanning the disclosed stimulator coil over the surface of the body in a raster pattern and measuring the impedance of the stimulating coil at each position throughout the scan, an image of the impedance of the circuit as a function of body position may be constructed. The principle is similar to that employed in the non-destructive testing of pipes, welds, and the like, wherein a coil is scanned over the surface of a conducting piece of metal [R. O. McCARY, D. W. Oliver, K. H. Silverstein, and D. J. Young. Eddy Current Imaging. IEEE Transactions on Magnetics MAG-20 (No. 5, September 1984): 1986-1988]. However, such non-destructive testing methods of imaging have not heretofore been applied to the imaging of biological tissue. Images may be made of the vector components of the impedance separately and/or of the magnitude of the impedance. If some region of the image corresponds to underlying tissue that has diminished electrical conductance (e.g., scar tissue, which may be an epileptic focus, or tissue in the vicinity of a blood clot), then the presence of that tissue will appear in the image as a region of unusual impedance. Because electrical impedance is a function of the frequency of alternating current through the coil, such images may be constructed for multiple or swept frequencies, and mixtures of such images may be used to better discriminate the biological structures that are being imaged. As an alternative to sweeping frequencies, a voltage pulse may be applied to the coil, and the Fourier components of its current response may be measured. In practice, measurement of changes of impedance (a spatial derivative of actual impedance) may generally best discriminate the biological structures, because the changes of impedance from one position in a scan to another may be small relative to total impedance and because position is the only variable that is being deliberately varied during the course of the scan. Such small impedance changes may be measured with bridge circuits that are nulled continuously throughout the scan. Furthermore, when the impedance changes are so small that they would be obscured by noise, the dwell time of measurement at individual locations in the raster may be increased, such that the measurement at each location is effectively an average of multiple measurements.

It is understood that other methods of imaging using the magnetic stimulator coil are also possible. For example, the coil may be used to actually electrically stimulate the tissue over a raster of locations, and currents induced in tissue by the stimulation may be measured through electrodes at fixed locations on the surface of the patient near the location of the raster of stimulations.

As an example, the scanning may be performed as shown in FIG. 10. A frame 101 similar to the base of a stereotaxic frame is rigidly attached to the head of the patient. An XY mechanical scanning stage is rigidly attached to the top of the frame. The XY scanning stage comprises two parts: a lower part 102 that is rigidly fixed to the frame 101 and an upper part 103 that can move independently in two directions relative to the lower part of the stage (front-to-back and side-to-side). The stimulator coil 30 is rigidly attached to the upper part of the XY scanning stage 103, with front-to-back axis attachment 104 and the side-to-side axis attachment 105. Thus, as the XY mechanical stage moves in the XY plane, the stimulator coil will move by the same distance in both the front-to-back and side-to-side directions.

It is understood that the scanning stage (102 plus 103) and stimulator coil 30 shown in FIG. 10 are connected via wires or cables to the circuits that respectively control motion of the stage and measure electrical impedance. The circuits that measure electrical impedance may be part of the impulse generator 310 in FIG. 1, or they may be dedicated circuits that communicate via wires, cables, or wireless technology to the device 300 in FIG. 1. The circuits that control movement of the stage may also be dedicated circuits that communicate via wires, cables, or wireless technology to the device 300 in FIG. 1, particularly its control unit 330, allowing that control unit to move the XY stage in a raster and acquire impedance measurements for each point in the raster.

The stimulator coil is also connected electrically to the scalp of the patient 100 through conducting material (e.g., conducting gel) as previously described (e.g., 29 in FIG. 7). If the area to be scanned is relatively small and the surface of the patient is flat over that area, the configuration shown in FIG. 10 may be used to perform the scan. However, if the scalp surface to be scanned exhibits significant curvature, the XY stage may be replaced by an XYZ stage that lifts and lowers the stimulator coil to accommodate the curvature. If the scalp surface to be scanned exhibits very significant curvature, the XY or XYZ stage may be replaced by a XYZ/tip/tilt stage or a hexapod positioning system, controlling motion with up to six degrees of freedom. All these types of positioning devices, along with their controllers, are commercially available [Publications "Nanopositioning/Piezoelectrics" and "Micropositioning". PI (Physik Instrumente) L.P., 16 Albert St., Auburn, Mass. 01501].

Constructing an image by the method disclosed above provides information about the electrical properties of the tissue underlying the scanning coil. If the structures are of the same order of magnitude in size as the head of the coil, then it might be possible to discern from the image what the biological structure is. Otherwise, inference of structure from the images may require processing of the images by methods that solve inverse-problems, for example using regularization techniques. The problem is related to that encountered in electrical impedance tomography, which measures the impedance of arrays of electrodes that are placed on the surface of the skin [David HOLDER. Brief introduction to bioimpedance and Introduction to biomedical electrical impedance tomography, in David S. Holder, ed. Electrical impedance tomography: methods, history, and applications. Bristol UK: Institute of Physics Publishing (2005), pp. 411-449]. However, the present disclosure differs from such previous tomographic methods in that the present invention measures the impedance of a toroidal magnetic stimulator coil that is electrically connected to the patient via a conducting gel or other conducting material, as shown for example in FIGS. 7 and 10.

However, even if it is not possible to discern a well-defined structure in the image, the image may nevertheless be useful because it may be used to subsequently re-position the stimulator to the same location that had been used previously for stimulation. Thus, an image may be generated on one day, followed by therapeutic stimulation performed with the stimulator positioned at the center of the image. If an image in the same general location of the scalp is acquired on another day, that image may not coincide spatially with the earlier image. However, by shifting and possibly rotating the earlier image relative to the later image, a best registration match between the images may be determined, for example, by least-squares or maximum likelihood criteria. Having determined the position in the second image that best corresponds to the center of the first image, the scanning stage may be used to move the scanning coil to that position, in order to re-stimulate at that particular position.

Use of this method to reposition the stimulator presupposes that the images will similar on different days, except for offsetting distances and angles, noise, and possibly average intensity that can be addressed by normalizing the images. However, if the underlying conducting biological structure has changed between images, that fact can be quantified by using the least-squares or maximum likelihood parameters that characterize the overall comparison between overlapping portions of the images produced on different days. Thus, if natural changes or changes that are due to an experimental intervention are occurring (e.g., due to drug treatment, or to stimulation using the disclosed stimulator), a comparison of the least-squares or maximum likelihood parameters that characterize differences between pairs of images can demonstrate the existence of conductance change in the underlying biological structures. Thus, measurement of bodily impedance changes with coils of the toroidal magnetic stimulation device may be used to monitor and quantify changes in the electrical conductance of target tissue.

Measurement of the coil's electrical impedance may be useful even when a scanned image is not being acquired, particularly in connection with the detection of motion and signal drift. Because of patient motion, e.g., due to the patient's fidgeting restlessness, muscular contractions and movement of the gel or other conducting material that is being used, there will inevitably be some motion of the magnetic stimulator coil relative to the location of the nerves or tissues that are the target of stimulation, no matter how rigidly the coil and conducting gel are comfortably held against the patient, using a strap or frame similar to those used for transcranial magnetic stimulation. Movement artifacts are not expected to be significant for the transcranial stimulation example shown in FIG. 10, but they might be a consideration for stimulation that is performed at other locations of the body.

For example, when stimulating the vagus nerve in the neck, motion may accompany the patient's breathing, involving contraction and an associated change in geometry of the sternocleidomastoid muscle that is situated close to the vagus nerve (identified as 65 in FIG. 7). In that case, by measuring the impedance of the stimulating coil (along with all the electrically conducting material with which the coil is in contact, including the patient), one may determine whether the impedance is changing as a function of the phase of the patient's respiration. If it is changing, the power of the stimulating coil may be modulated in such a way as to maintain the induced electrical field in the vicinity of the vagus nerve nearly constant, as evidenced, for example, by a respiration-independent physiological response on the part of the patient. It may also be therapeutically advantageous to program the control unit 330 of FIG. 1 to control the impulse generator 310 of FIG. 1 in such a way as to temporally modulate stimulation by the magnetic stimulator coil 340 in FIG. 1, in order to enhance a physiological response that occurs preferentially during a particular phase of respiration. To do so, the control unit estimates the phase of the patient's respiration from the changing measured impedance, then preferentially stimulates during particular respiratory phases.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Furthermore, it is understood that the low-current toroidal magnetic stimulation device that is disclosed herein may also be used for all other applications in which a higher-current magnetic stimulator is used, including (but not limited to) those described in the publication: Chris HOVEY and Reza Jalinous. The Guide to Magnetic Stimulation. The Magstim Company Ltd, Spring Gardens, Whitland, Carmarthenshire, SA34 0HR, United Kingdom. Those applications pertain to Motor Evoked Potentials (MEPs), Facilitation, MEP Variability, Central Motor Conduction Time (CMCT), Corticomotor Threshold, Response amplitude, Demyelinating Neuropathies, Magnetic Pulse Pairs, Brain Mapping, Sensory Evoked Potentials (SEPs), Motor Evoked Potentials (MEPs), Facilitation, MEP Variability, Central Motor Conduction Time (CMCT), Corticomotor Threshold, Response amplitude, Demyelinating Neuropathies, Magnetic Pulse Pairs, Brain Mapping, Sensory Evoked Potentials, Coma, Drug Monitoring, Epilepsy, Facial Nerve, Spinal nerve roots, Motor Neurone Disease, Movement Disorders, Dystonia, Huntington's Disease, Myoclonus, Parkinson's Disease, Tremor, Tourette Syndrome, Multiple Sclerosis, Neuroscience, Operating Room Monitoring, Pain, Peripheral Nerves, Plasticity, Psychiatry, Depression, Mania, Schizophrenia, Psychology, Rehabilitation, Muscle injury, Relief of Spasticity, Simulation of a Cough, Urology, Spinal Injuries, Cervical Spondylosis, Sports Medicine, Stroke, Thoracic Medicine, Phrenic Nerve Stimulation, and Urology.

The invention claimed is:

1. A device for selectively applying energy to a target region in a patient, the device comprising:
a power source configured to generate a magnetic field outside of the patient;
a housing containing an enclosed coil and an electrically conductive fluid surrounding at least a portion of the enclosed coil; and
wherein the enclosed coil is configured to transmit the magnetic field through an outer skin surface of the patient such that the magnetic field induces an electric current at a nerve at the target region within the patient, wherein the electric current comprises bursts of electrical impulses, wherein each of the electrical impulses comprises a duration from about 50 microseconds to about 1000 microseconds, wherein each of the bursts comprises a frequency from about 15 Hz to about 50 Hz, wherein the electric current is sufficient to modulate the nerve.

2. The device of claim 1, wherein the target region is a nerve at least 1 cm below the outer skin surface.

3. The device of claim 1, wherein the target region is a nerve at least 2 cm below the outer skin surface.

4. The device of claim 1, further comprising:
a second enclosed coil positioned adjacent to or near the enclosed coil, and wherein the power source is configured to generate a second magnetic field within the second enclosed coil.

5. The device of claim 1, further comprising:
an electrical insulator positioned around a portion of the enclosed coil such that a component of the electric current normal to a surface of the insulator is zero.

6. The device of claim 1, wherein the enclosed coil is configured to induce an electric field at the target region, wherein the electric field allows the electric current to flow through the outer skin surface of the patient.

7. The device of claim 1, wherein each of the electrical impulses comprises a duration from about 50 microseconds to about 400 microseconds.

8. The device of claim 1, wherein the nerve is a vagus nerve.

9. The device of claim 1, further comprising:
an electrically conductive contact surface coupled to the enclosed coil, wherein the electrically conductive contact surface is configured to transmit the magnetic field through a skin surface of a neck of the patient to a vagus nerve of the patient.

10. The device of claim 1, wherein the housing comprises a handheld device with an interior, and wherein the enclosed coil is substantially surrounded by the electrically conductive fluid within the interior.

11. The device of claim 1, wherein the electrically conductive fluid comprises an electrically conductive gel.

12. The device of claim 1, wherein the electrically conductive fluid comprises an electrically conductive liquid.

13. A method comprising:
applying an energy selectively to a target region within a patient, wherein the applying is via a device comprising a power source and a housing, wherein the power source generates a magnetic field outside of the patient, wherein the housing contains an enclosed coil and an electrically conductive fluid surrounding at least a portion of the enclosed coil, wherein the enclosed coil transmits the magnetic field through an outer skin surface of the patient such that the magnetic field induces an electric current at a nerve at the target region within the patient, wherein the electric current comprises bursts of electrical impulses, wherein each of the electrical impulses comprises a duration from about 50 microseconds to about 1000 microseconds, wherein each of the bursts comprises a frequency from about 15 Hz to about 50 Hz, wherein the electric current is sufficient to modulate the nerve.

* * * * *

UNITED STATES PATENT AND TRADEMARK OFFICE
CERTIFICATE OF CORRECTION

PATENT NO.        : 9,233,258 B2
APPLICATION NO.   : 14/636498
DATED             : January 12, 2016
INVENTOR(S)       : Bruce J. Simon et al.

Page 1 of 1

It is certified that error appears in the above-identified patent and that said Letters Patent is hereby corrected as shown below:

Title Page, item (72) should read

John T. Raffle, Austin, TX (US)

Signed and Sealed this
Nineteenth Day of July, 2016

Michelle K. Lee
*Director of the United States Patent and Trademark Office*